United States Patent
Goodnow et al.

(10) Patent No.: US 8,115,635 B2
(45) Date of Patent: *Feb. 14, 2012

(54) RF TAG ON TEST STRIPS, TEST STRIP VIALS AND BOXES

(75) Inventors: Timothy T. Goodnow, Pleasanton, CA (US); Lei (Lawrence) He, Moraga, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/625,528

(22) Filed: Nov. 24, 2009

(65) Prior Publication Data
US 2010/0148972 A1    Jun. 17, 2010

Related U.S. Application Data

(63) Continuation of application No. 12/476,921, filed on Jun. 2, 2009, which is a continuation of application No. 11/350,398, filed on Feb. 7, 2006, now Pat. No. 7,545,272.

(60) Provisional application No. 60/701,654, filed on Jul. 21, 2005, provisional application No. 60/650,912, filed on Feb. 8, 2005.

(51) Int. Cl.
*G08B 13/14* (2006.01)

(52) U.S. Cl. .............. 340/572.1; 340/572.8; 340/573.1; 600/347

(58) Field of Classification Search ............... 340/572.1, 340/572.8, 573.1, 572.2, 573.4, 539.1, 539.17, 340/568.1; 422/82.01; 600/365, 347; 204/403.1
See application file for complete search history.

(56) References Cited

U.S. PATENT DOCUMENTS

| | | | |
|---|---|---|---|
| 3,623,091 A | 11/1971 | Mayo et al. |
| 3,634,756 A | 1/1972 | Carlise |
| 3,750,167 A | 7/1973 | Gehman et al. |
| 3,774,243 A | 11/1973 | Ng et al. |
| 3,861,397 A | 1/1975 | Rao et al. |
| 3,872,455 A | 3/1975 | Fuller et al. |
| 3,937,214 A | 2/1976 | Hutchins |
| 4,025,791 A | 5/1977 | Lennington et al. |
| 4,075,632 A | 2/1978 | Baldwin et al. |
| 4,121,102 A | 10/1978 | Wilson |

(Continued)

FOREIGN PATENT DOCUMENTS
AU    773812    6/2004
(Continued)

OTHER PUBLICATIONS

European Patent Application No. EP-06720461.0, Supplementary European Search Report and European Search Opinion mailed May 28, 2010.

(Continued)

*Primary Examiner* — Anh V La
(74) *Attorney, Agent, or Firm* — Jackson & Co., LLP

(57) ABSTRACT

A glucose monitoring system, includes a glucose sensor strip or package of strips. The strip includes a substrate and a glucose monitoring circuit that has electrodes and a bodily fluid application portion of selected chemical composition. An antenna is integrated with the glucose sensor strip. A RFID sensor chip is coupled with the glucose sensor strip and the antenna. The chip has a memory containing digitally-encoded data representing calibration and/or expiration date information for the strip.

24 Claims, 9 Drawing Sheets

U.S. PATENT DOCUMENTS

| | | |
|---|---|---|
| 4,129,855 A | 12/1978 | Rodrian |
| 4,170,311 A | 10/1979 | Spaw |
| 4,207,468 A | 6/1980 | Wilson |
| 4,224,125 A | 9/1980 | Nakamura et al. |
| 4,237,900 A | 12/1980 | Schulman et al. |
| 4,308,520 A | 12/1981 | Darlington |
| 4,417,157 A | 11/1983 | Gershberg et al. |
| 4,431,004 A | 2/1984 | Bessman et al. |
| 4,432,360 A | 2/1984 | Mumford et al. |
| 4,470,047 A | 9/1984 | Vogt et al. |
| 4,475,481 A | 10/1984 | Carroll |
| 4,490,464 A | 12/1984 | Gorton et al. |
| 4,494,950 A | 1/1985 | Fischell |
| 4,507,652 A | 3/1985 | Vogt et al. |
| 4,556,063 A | 12/1985 | Thompson et al. |
| 4,561,443 A | 12/1985 | Hogrefe et al. |
| 4,568,335 A | 2/1986 | Updike et al. |
| 4,581,336 A | 4/1986 | Malloy et al. |
| RE32,361 E | 2/1987 | Duggan |
| 4,679,562 A | 7/1987 | Luksha |
| 4,681,111 A | 7/1987 | Silvian |
| 4,703,756 A | 11/1987 | Gough et al. |
| 4,724,427 A | 2/1988 | Carroll |
| 4,725,841 A | 2/1988 | Nysen et al. |
| 4,730,500 A | 3/1988 | Hughes |
| 4,734,698 A | 3/1988 | Nysen et al. |
| 4,757,022 A | 7/1988 | Shults et al. |
| 4,814,595 A | 3/1989 | Gilboa |
| 4,827,395 A | 5/1989 | Anders et al. |
| 4,857,893 A | 8/1989 | Carroll |
| 4,916,441 A | 4/1990 | Gombrich |
| 4,944,299 A | 7/1990 | Silvian |
| 4,947,407 A | 8/1990 | Silvian |
| 4,987,897 A | 1/1991 | Funke |
| 4,994,167 A | 2/1991 | Shults et al. |
| 5,012,236 A | 4/1991 | Troyk et al. |
| 5,077,547 A | 12/1991 | Burgmann |
| 5,084,699 A | 1/1992 | DeMichele |
| 5,095,309 A | 3/1992 | Troyk et al. |
| 5,117,825 A | 6/1992 | Grevious |
| 5,127,404 A | 7/1992 | Wyborny et al. |
| 5,153,583 A | 10/1992 | Murdoch |
| 5,156,972 A | 10/1992 | Issachar |
| 5,161,532 A | 11/1992 | Joseph |
| 5,211,129 A | 5/1993 | Taylor et al. |
| 5,217,011 A | 6/1993 | Bisch |
| 5,228,449 A | 7/1993 | Christ et al. |
| 5,235,326 A | 8/1993 | Beigel et al. |
| 5,235,980 A | 8/1993 | Varrichio et al. |
| 5,241,961 A | 9/1993 | Henry |
| 5,245,332 A | 9/1993 | Katzenstein |
| 5,250,944 A | 10/1993 | Urbas et al. |
| 5,252,962 A | 10/1993 | Urbas et al. |
| 5,252,979 A | 10/1993 | Nysen |
| 5,258,766 A | 11/1993 | Murdoch |
| 5,262,772 A | 11/1993 | Urbas et al. |
| 5,292,343 A | 3/1994 | Blanchette et al. |
| 5,312,446 A | 5/1994 | Holschbach et al. |
| 5,314,450 A | 5/1994 | Thompson |
| 5,322,063 A | 6/1994 | Allen et al. |
| 5,332,315 A | 7/1994 | Baker et al. |
| 5,335,246 A | 8/1994 | Yokev et al. |
| 5,336,245 A | 8/1994 | Adams et al. |
| 5,341,128 A | 8/1994 | Keyser et al. |
| 5,349,852 A | 9/1994 | Kamen et al. |
| 5,350,412 A | 9/1994 | Hoegnelid et al. |
| 5,354,319 A | 10/1994 | Wyborny et al. |
| 5,355,137 A | 10/1994 | Schurmann |
| 5,357,427 A | 10/1994 | Langen et al. |
| 5,368,028 A | 11/1994 | Palti |
| 5,372,133 A | 12/1994 | Hogen |
| 5,373,301 A | 12/1994 | Bowers et al. |
| 5,376,070 A | 12/1994 | Purvis et al. |
| 5,378,332 A | 1/1995 | Pandey |
| 5,390,671 A | 2/1995 | Lord et al. |
| 5,415,181 A | 5/1995 | Hogrefe et al. |
| 5,422,636 A | 6/1995 | Urbas et al. |
| 5,423,334 A | 6/1995 | Jordan |
| 5,430,447 A | 7/1995 | Meier |
| 5,451,839 A | 9/1995 | Rappaport et al. |
| 5,458,122 A | 10/1995 | Hethuin |
| 5,462,051 A | 10/1995 | Oka et al. |
| 5,466,246 A | 11/1995 | Silvian |
| 5,472,317 A | 12/1995 | Field et al. |
| 5,476,488 A | 12/1995 | Morgan et al. |
| 5,489,414 A | 2/1996 | Schreiber et al. |
| 5,497,772 A | 3/1996 | Schulman et al. |
| 5,511,553 A | 4/1996 | Segalowitz |
| 5,519,262 A | 5/1996 | Wood |
| 5,521,602 A | 5/1996 | Carroll et al. |
| 5,526,844 A | 6/1996 | Kamen et al. |
| 5,532,686 A | 7/1996 | Urbas et al. |
| 5,533,389 A | 7/1996 | Kamen et al. |
| 5,541,851 A | 7/1996 | Sato et al. |
| 5,548,728 A | 8/1996 | Danknick |
| 5,558,638 A | 9/1996 | Evers et al. |
| 5,579,001 A | 11/1996 | Dempsey et al. |
| 5,579,775 A | 12/1996 | Dempsey et al. |
| 5,601,435 A | 2/1997 | Quy |
| 5,626,630 A | 5/1997 | Markowitz et al. |
| 5,629,678 A | 5/1997 | Gargano et al. |
| 5,630,216 A | 5/1997 | McEwan |
| 5,630,836 A | 5/1997 | Prem et al. |
| 5,632,272 A | 5/1997 | Diab et al. |
| 5,634,468 A | 6/1997 | Platt et al. |
| 5,638,832 A | 6/1997 | Singer et al. |
| 5,654,693 A | 8/1997 | Cocita |
| 5,660,163 A | 8/1997 | Schulman et al. |
| 5,665,065 A | 9/1997 | Colman et al. |
| 5,683,432 A | 11/1997 | Goedeke et al. |
| 5,687,734 A | 11/1997 | Dempsey et al. |
| 5,689,239 A | 11/1997 | Turner et al. |
| 5,696,485 A | 12/1997 | Trehame |
| 5,697,958 A | 12/1997 | Paul et al. |
| 5,704,352 A | 1/1998 | Tremblay et al. |
| 5,707,502 A | 1/1998 | McCaffrey et al. |
| 5,718,234 A | 2/1998 | Warden et al. |
| 5,722,999 A | 3/1998 | Snell |
| 5,724,030 A | 3/1998 | Urbas et al. |
| 5,725,578 A | 3/1998 | Knapp et al. |
| D393,313 S | 4/1998 | Meisner et al. |
| 5,735,285 A | 4/1998 | Albert et al. |
| 5,741,314 A | 4/1998 | Daly et al. |
| 5,749,907 A | 5/1998 | Mann |
| 5,752,977 A | 5/1998 | Grevious et al. |
| 5,759,199 A | 6/1998 | Snell et al. |
| 5,764,034 A | 6/1998 | Bowman et al. |
| 5,766,232 A | 6/1998 | Grevious et al. |
| 5,767,792 A | 6/1998 | Urbas |
| 5,769,876 A | 6/1998 | Silvian |
| 5,771,438 A | 6/1998 | Palermo et al. |
| 5,772,586 A | 6/1998 | Heinonen et al. |
| 5,785,043 A | 7/1998 | Cyrus et al. |
| 5,791,342 A | 8/1998 | Woodard |
| 5,791,344 A | 8/1998 | Schulman et al. |
| 5,792,207 A | 8/1998 | Dietrich |
| 5,804,047 A | 9/1998 | Karube et al. |
| 5,809,059 A | 9/1998 | Souissi et al. |
| 5,821,854 A | 10/1998 | Dorinski et al. |
| 5,822,715 A | 10/1998 | Worthington et al. |
| 5,832,448 A | 11/1998 | Brown |
| 5,833,603 A | 11/1998 | Kovacs et al. |
| 5,842,118 A | 11/1998 | Wood, Jr. |
| 5,847,551 A | 12/1998 | Arora et al. |
| 5,856,809 A | 1/1999 | Schoepfer |
| 5,859,873 A | 1/1999 | Ritter |
| 5,861,018 A | 1/1999 | Feierbach |
| 5,862,517 A | 1/1999 | Honey et al. |
| 5,868,669 A | 2/1999 | Iliff |
| 5,873,070 A | 2/1999 | Bunte et al. |
| 5,882,300 A | 3/1999 | Malinouskas et al. |
| 5,894,266 A | 4/1999 | Wood et al. |
| 5,896,060 A | 4/1999 | Ovard et al. |
| 5,899,855 A | 5/1999 | Brown |
| 5,902,234 A | 5/1999 | Webb |
| 5,904,708 A | 5/1999 | Goedeke |
| 5,916,237 A | 6/1999 | Schu |

| | | | | | | |
|---|---|---|---|---|---|---|
| 5,917,414 A | 6/1999 | Oppelt et al. | | 6,230,059 B1 | 5/2001 | Duffin |
| 5,918,603 A | 7/1999 | Brown | | 6,232,891 B1 | 5/2001 | Rosenberg |
| 5,919,214 A | 7/1999 | Ciciarelli et al. | | 6,233,471 B1 | 5/2001 | Berner et al. |
| 5,925,021 A | 7/1999 | Castellano et al. | | 6,233,532 B1 | 5/2001 | Boudreau et al. |
| 5,931,873 A | 8/1999 | Cisar | | 6,233,539 B1 | 5/2001 | Brown |
| 5,935,078 A | 8/1999 | Feierbach | | 6,234,006 B1 | 5/2001 | Sunshine et al. |
| 5,956,501 A | 9/1999 | Brown | | 6,236,888 B1 | 5/2001 | Thompson |
| 5,959,371 A | 9/1999 | Dooley et al. | | 6,238,813 B1 | 5/2001 | Maile et al. |
| 5,959,529 A | 9/1999 | Kail, IV | | 6,240,318 B1 | 5/2001 | Phillips |
| 5,960,403 A | 9/1999 | Brown | | 6,243,012 B1 | 6/2001 | Shober et al. |
| 5,961,451 A | 10/1999 | Reber et al. | | 6,245,215 B1 | 6/2001 | Douglas et al. |
| 5,963,132 A | 10/1999 | Yoakum | | 6,246,992 B1 | 6/2001 | Brown |
| 5,963,650 A | 10/1999 | Simionescu et al. | | 6,248,067 B1 | 6/2001 | Causey, III et al. |
| 5,974,397 A | 10/1999 | Olsson et al. | | 6,249,703 B1 | 6/2001 | Stanton et al. |
| 5,986,962 A | 11/1999 | Bertin et al. | | 6,249,809 B1 | 6/2001 | Bro |
| 5,997,476 A | 12/1999 | Brown | | 6,250,309 B1 | 6/2001 | Krichen et al. |
| 5,999,849 A | 12/1999 | Gord et al. | | 6,252,389 B1 | 6/2001 | Baba et al. |
| 5,999,857 A | 12/1999 | Weijand et al. | | 6,254,548 B1 | 7/2001 | Ishikawa et al. |
| 6,001,239 A | 12/1999 | Douglas et al. | | 6,259,382 B1 | 7/2001 | Rosenberg |
| 6,002,994 A | 12/1999 | Lane et al. | | 6,259,937 B1 | 7/2001 | Schulman et al. |
| 6,014,578 A | 1/2000 | Minoz | | 6,263,194 B1 | 7/2001 | Chan et al. |
| 6,014,765 A | 1/2000 | Maeda et al. | | 6,263,245 B1 | 7/2001 | Snell |
| 6,022,315 A | 2/2000 | Iliff | | 6,263,247 B1 | 7/2001 | Mueller et al. |
| 6,023,641 A | 2/2000 | Thompson | | 6,270,457 B1 | 8/2001 | Bardy |
| 6,032,064 A | 2/2000 | Devlin et al. | | 6,272,364 B1 | 8/2001 | Kurnik |
| 6,032,119 A | 2/2000 | Brown et al. | | 6,277,072 B1 | 8/2001 | Bardy |
| 6,037,879 A | 3/2000 | Tuttle | | 6,280,380 B1 | 8/2001 | Bardy |
| 6,050,940 A | 4/2000 | Braun et al. | | 6,283,761 B1 | 9/2001 | Joao |
| 6,057,758 A | 5/2000 | Dempsey et al. | | 6,285,897 B1 | 9/2001 | Kilcoyne et al. |
| 6,085,576 A | 7/2000 | Sunshine et al. | | 6,287,252 B1 | 9/2001 | Lugo |
| 6,087,837 A | 7/2000 | Chase | | 6,289,209 B1 | 9/2001 | Wood, Jr. |
| 6,088,608 A | 7/2000 | Schulman et al. | | 6,289,237 B1 | 9/2001 | Mickle et al. |
| 6,091,987 A | 7/2000 | Thompson | | 6,289,244 B1 | 9/2001 | Conley et al. |
| 6,092,530 A | 7/2000 | Weissman et al. | | 6,291,200 B1 | 9/2001 | LeJeune et al. |
| 6,093,146 A | 7/2000 | Filangeri | | 6,293,925 B1 | 9/2001 | Safabash et al. |
| 6,100,804 A | 8/2000 | Brady et al. | | 6,294,281 B1 | 9/2001 | Heller |
| 6,104,333 A | 8/2000 | Wood, Jr. | | 6,294,997 B1 | 9/2001 | Paratore et al. |
| 6,107,910 A | 8/2000 | Nysen | | 6,295,473 B1 | 9/2001 | Rosar |
| 6,115,636 A | 9/2000 | Ryan | | 6,297,723 B1 | 10/2001 | Shoji et al. |
| 6,120,676 A | 9/2000 | Heller et al. | | 6,298,255 B1 | 10/2001 | Cordero et al. |
| 6,128,520 A | 10/2000 | Minoz | | 6,298,271 B1 | 10/2001 | Weijand |
| 6,130,602 A | 10/2000 | O'Toole et al. | | 6,312,393 B1 | 11/2001 | Abreu |
| 6,130,623 A | 10/2000 | MacLellan et al. | | 6,319,200 B1 | 11/2001 | Lai et al. |
| 6,132,371 A | 10/2000 | Dempsey et al. | | 6,323,772 B1 | 11/2001 | Lake |
| 6,134,459 A | 10/2000 | Roberts et al. | | 6,324,426 B1 | 11/2001 | Thompson |
| 6,135,970 A | 10/2000 | Kadhiresan et al. | | 6,326,160 B1 | 12/2001 | Dunn et al. |
| 6,141,584 A | 10/2000 | Rockwell et al. | | 6,329,161 B1 | 12/2001 | Heller et al. |
| 6,144,866 A | 11/2000 | Miesel et al. | | 6,329,929 B1 | 12/2001 | Weijand et al. |
| 6,144,871 A | 11/2000 | Saito et al. | | 6,336,900 B1 | 1/2002 | Alleckson et al. |
| 6,147,618 A | 11/2000 | Halleck et al. | | 6,345,203 B1 | 2/2002 | Mueller et al. |
| 6,159,147 A | 12/2000 | Lichter et al. | | 6,348,640 B1 | 2/2002 | Navot et al. |
| 6,160,536 A | 12/2000 | Forest | | 6,351,630 B2 | 2/2002 | Wood, Jr. |
| 6,163,260 A | 12/2000 | Conwell et al. | | 6,353,406 B1 | 3/2002 | Lanzl et al. |
| 6,163,721 A | 12/2000 | Thompson | | 6,353,761 B1 | 3/2002 | Conley et al. |
| 6,165,142 A | 12/2000 | Bar | | 6,356,776 B1 | 3/2002 | Berner et al. |
| 6,167,303 A | 12/2000 | Thompson | | 6,359,444 B1 | 3/2002 | Grimes |
| 6,167,358 A | 12/2000 | Othmer et al. | | 6,360,888 B1 | 3/2002 | McIvor et al. |
| 6,168,563 B1 | 1/2001 | Brown | | 6,363,282 B1 | 3/2002 | Nichols et al. |
| 6,169,925 B1 | 1/2001 | Villaseca et al. | | 6,366,794 B1 | 4/2002 | Moussy et al. |
| 6,175,752 B1 | 1/2001 | Say et al. | | 6,369,694 B1 | 4/2002 | Mejia |
| 6,185,452 B1 | 2/2001 | Schulman et al. | | 6,374,079 B1 | 4/2002 | Hsu |
| 6,185,454 B1 | 2/2001 | Thompson | | 6,377,185 B1 | 4/2002 | Halleck et al. |
| 6,185,460 B1 | 2/2001 | Thompson | | 6,379,301 B1 | 4/2002 | Worthington et al. |
| 6,198,123 B1 | 3/2001 | Linder et al. | | 6,381,491 B1 | 4/2002 | Maile et al. |
| 6,198,952 B1 | 3/2001 | Miesel | | 6,381,496 B1 | 4/2002 | Meadows et al. |
| 6,200,264 B1 | 3/2001 | Satherley et al. | | 6,387,048 B1 | 5/2002 | Schulman et al. |
| 6,200,265 B1 | 3/2001 | Walsh et al. | | 6,389,315 B1 | 5/2002 | Schu et al. |
| 6,200,772 B1 | 3/2001 | Vadgama et al. | | 6,393,318 B1 | 5/2002 | Conn et al. |
| 6,201,980 B1 | 3/2001 | Darrow et al. | | 6,396,416 B1 | 5/2002 | Kuusela et al. |
| 6,206,835 B1 | 3/2001 | Spillman, Jr. et al. | | 6,398,727 B1 | 6/2002 | Bui et al. |
| 6,212,416 B1 | 4/2001 | Ward et al. | | 6,400,338 B1 | 6/2002 | Mejia et al. |
| 6,212,431 B1 | 4/2001 | Hahn et al. | | 6,400,974 B1 | 6/2002 | Lesho |
| 6,216,038 B1 | 4/2001 | Hartlaub et al. | | 6,405,066 B1 | 6/2002 | Essenpreis et al. |
| 6,221,011 B1 | 4/2001 | Bardy | | 6,406,426 B1 | 6/2002 | Reuss et al. |
| 6,223,080 B1 | 4/2001 | Thompson | | 6,412,977 B1 | 7/2002 | Black et al. |
| 6,223,083 B1 | 4/2001 | Rosar | | 6,413,393 B1 | 7/2002 | Van Antwerp et al. |
| 6,225,901 B1 | 5/2001 | Kail, IV | | 6,416,471 B1 | 7/2002 | Kumar et al. |
| 6,228,057 B1 | 5/2001 | Vasko | | 6,418,346 B1 | 7/2002 | Nelson et al. |
| 6,229,454 B1 | 5/2001 | Heikkila et al. | | 6,418,783 B2 | 7/2002 | Sunshine et al. |

| | | |
|---|---|---|
| 6,424,820 B1 | 7/2002 | Burdick et al. |
| 6,427,088 B1 | 7/2002 | Bowman, IV et al. |
| 6,428,475 B1 | 8/2002 | Shen |
| 6,433,671 B1 | 8/2002 | Nysen |
| 6,434,425 B1 | 8/2002 | Thompson |
| 6,434,429 B1 | 8/2002 | Kraus et al. |
| 6,438,422 B1 | 8/2002 | Schu et al. |
| 6,441,747 B1 | 8/2002 | Khair et al. |
| 6,442,432 B2 | 8/2002 | Lee |
| 6,442,433 B1 | 8/2002 | Linberg |
| 6,442,434 B1 | 8/2002 | Zarinetchi et al. |
| 6,443,891 B1 | 9/2002 | Grevious |
| 6,447,448 B1 | 9/2002 | Ishikawa et al. |
| 6,450,953 B1 | 9/2002 | Place et al. |
| 6,453,196 B1 | 9/2002 | Von Arx et al. |
| 6,453,198 B1 | 9/2002 | Torgerson et al. |
| 6,454,708 B1 | 9/2002 | Ferguson et al. |
| 6,456,256 B1 | 9/2002 | Amundson et al. |
| 6,458,080 B1 | 10/2002 | Brown et al. |
| 6,459,882 B1 | 10/2002 | Palermo et al. |
| 6,466,771 B2 | 10/2002 | Wood, Jr. |
| 6,466,810 B1 | 10/2002 | Ward et al. |
| 6,467,003 B1 | 10/2002 | Doerenberg et al. |
| 6,470,215 B1 | 10/2002 | Kraus et al. |
| 6,472,991 B1 | 10/2002 | Schulman et al. |
| 6,480,745 B2 | 11/2002 | Nelson et al. |
| 6,482,156 B2 | 11/2002 | Iliff |
| 6,483,473 B1 | 11/2002 | King et al. |
| 6,485,461 B1 | 11/2002 | Mason et al. |
| 6,490,487 B1 | 12/2002 | Kraus et al. |
| 6,495,892 B2 | 12/2002 | Goodman et al. |
| 6,496,729 B2 | 12/2002 | Thompson |
| 6,497,655 B1 | 12/2002 | Linberg et al. |
| 6,509,588 B1 | 1/2003 | O'Phelan et al. |
| 6,511,814 B1 | 1/2003 | Carpenter |
| 6,512,944 B1 | 1/2003 | Kovtun et al. |
| 6,515,919 B1 | 2/2003 | Lee |
| 6,522,296 B2 | 2/2003 | Holt et al. |
| 6,522,525 B1 | 2/2003 | O'Phelan et al. |
| 6,525,330 B2 | 2/2003 | Paolini et al. |
| 6,525,648 B1 | 2/2003 | Kubler et al. |
| 6,526,144 B2 | 2/2003 | Markandey et al. |
| 6,527,712 B1 | 3/2003 | Brown et al. |
| 6,529,127 B2 | 3/2003 | Townsend et al. |
| 6,531,957 B1 | 3/2003 | Nysen |
| 6,539,249 B1 | 3/2003 | Kadhiresan et al. |
| 6,539,253 B2 | 3/2003 | Thompson et al. |
| 6,542,231 B1 | 4/2003 | Garrett |
| 6,544,173 B2 | 4/2003 | West et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,549,796 B2 | 4/2003 | Sohrab |
| 6,551,842 B1 | 4/2003 | Carpenter |
| 6,553,336 B1 | 4/2003 | Johnson et al. |
| 6,556,140 B2 | 4/2003 | East |
| 6,556,871 B2 | 4/2003 | Schmitt et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,571,126 B1 | 5/2003 | O'Phelan et al. |
| 6,571,128 B2 | 5/2003 | Lebel et al. |
| 6,571,617 B2 | 6/2003 | Van Niekerk et al. |
| 6,574,510 B2 | 6/2003 | Von Arx et al. |
| 6,574,511 B2 | 6/2003 | Lee |
| 6,577,899 B2 | 6/2003 | Lebel et al. |
| 6,577,901 B2 | 6/2003 | Thompson |
| 6,579,690 B1 | 6/2003 | Bonnecaze et al. |
| 6,580,358 B1 | 6/2003 | Nysen |
| 6,582,365 B1 | 6/2003 | Hines et al. |
| 6,585,644 B2 | 7/2003 | Lebel et al. |
| 6,590,395 B2 | 7/2003 | Reykowski et al. |
| 6,592,518 B2 | 7/2003 | Denker et al. |
| 6,594,514 B2 | 7/2003 | Berner et al. |
| 6,595,919 B2 | 7/2003 | Berner et al. |
| 6,602,678 B2 | 8/2003 | Kwon et al. |
| 6,606,566 B1 | 8/2003 | Sunshine |
| 6,607,485 B2 | 8/2003 | Bardy |
| 6,607,509 B2 | 8/2003 | Bobroff et al. |
| 6,611,224 B1 | 8/2003 | Nysen et al. |
| 6,614,406 B2 | 9/2003 | Amundson et al. |
| 6,615,074 B2 | 9/2003 | Mickle et al. |
| 6,615,483 B2 | 9/2003 | Lindegren |
| 6,617,963 B1 | 9/2003 | Watters et al. |
| 6,622,044 B2 | 9/2003 | Bange et al. |
| 6,623,501 B2 | 9/2003 | Heller et al. |
| 6,623,619 B2 | 9/2003 | Saffell et al. |
| 6,627,154 B1 | 9/2003 | Goodman et al. |
| 6,628,985 B2 | 9/2003 | Sweeney et al. |
| 6,628,989 B1 | 9/2003 | Penner et al. |
| 6,630,910 B2 | 10/2003 | Forster et al. |
| 6,633,772 B2 | 10/2003 | Ford et al. |
| 6,635,167 B1 | 10/2003 | Batman et al. |
| 6,636,161 B2 | 10/2003 | Rosenberg |
| 6,641,533 B2 | 11/2003 | Causey, III et al. |
| 6,641,541 B1 | 11/2003 | Lovett et al. |
| 6,643,278 B1 | 11/2003 | Panasik et al. |
| 6,648,821 B2 | 11/2003 | Lebel et al. |
| 6,648,823 B2 | 11/2003 | Thompson |
| 6,652,720 B1 | 11/2003 | Mansouri et al. |
| 6,656,114 B1 | 12/2003 | Poulsen et al. |
| 6,656,117 B2 | 12/2003 | Jentsch et al. |
| 6,656,158 B2 | 12/2003 | Gregory et al. |
| 6,656,159 B2 | 12/2003 | Flaherty |
| 6,659,948 B2 | 12/2003 | Lebel et al. |
| 6,662,048 B2 | 12/2003 | Balczewski et al. |
| 6,662,439 B1 | 12/2003 | Bhullar |
| 6,668,196 B1 | 12/2003 | Villegas et al. |
| 6,669,669 B2 | 12/2003 | Flaherty et al. |
| 6,675,045 B2 | 1/2004 | Mass et al. |
| 6,675,049 B2 | 1/2004 | Thompson et al. |
| 6,681,003 B2 | 1/2004 | Linder et al. |
| 6,682,480 B1 | 1/2004 | Habib et al. |
| 6,687,118 B1 | 2/2004 | O'Phelan et al. |
| 6,687,546 B2 | 2/2004 | Lebel et al. |
| 6,692,446 B2 | 2/2004 | Hoek |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,699,265 B1 | 3/2004 | O'Phelan et al. |
| 6,702,857 B2 | 3/2004 | Brauker et al. |
| 6,705,991 B2 | 3/2004 | Bardy |
| 6,708,065 B2 | 3/2004 | Von Arx et al. |
| 6,719,689 B2 | 4/2004 | Munneke et al. |
| 6,720,930 B2 | 4/2004 | Johnson et al. |
| 6,723,046 B2 | 4/2004 | Lichtenstein et al. |
| 6,723,072 B2 | 4/2004 | Mahoney et al. |
| 6,731,976 B2 | 5/2004 | Penn et al. |
| 6,733,446 B2 | 5/2004 | Lebel et al. |
| 6,733,495 B1 | 5/2004 | Bek et al. |
| 6,734,802 B2 | 5/2004 | Halleck et al. |
| 6,735,551 B2 | 5/2004 | Voegeli et al. |
| 6,736,770 B2 | 5/2004 | Leysieffer et al. |
| 6,738,654 B2 | 5/2004 | Sohrab |
| 6,738,670 B2 | 5/2004 | Almendinger et al. |
| 6,738,671 B2 | 5/2004 | Christophersom et al. |
| 6,740,033 B1 | 5/2004 | Olejniczak et al. |
| 6,740,059 B2 | 5/2004 | Flaherty |
| 6,740,075 B2 | 5/2004 | Lebel et al. |
| 6,741,877 B1 | 5/2004 | Shults et al. |
| 6,745,077 B1 | 6/2004 | Griffith et al. |
| 6,746,960 B2 | 6/2004 | Goodman |
| 6,749,566 B2 | 6/2004 | Russ |
| 6,749,587 B2 | 6/2004 | Flaherty |
| 6,752,299 B2 | 6/2004 | Shetler et al. |
| 6,755,783 B2 | 6/2004 | Cosentino et al. |
| 6,757,523 B2 | 6/2004 | Fry |
| 6,758,810 B2 | 7/2004 | Lebel et al. |
| 6,763,269 B2 | 7/2004 | Cox |
| 6,768,425 B2 | 7/2004 | Flaherty et al. |
| 6,775,046 B2 | 8/2004 | Hill et al. |
| 6,781,508 B2 | 8/2004 | Tuttle et al. |

| | | | | | | |
|---|---|---|---|---|---|---|
| 6,784,813 B2 | 8/2004 | Shanks et al. | | 6,997,388 B2 | 2/2006 | Yogev et al. |
| 6,788,973 B2 | 9/2004 | Davis et al. | | 6,997,907 B2 | 2/2006 | Safabash et al. |
| 6,795,735 B2 | 9/2004 | Esler | | 6,998,247 B2 | 2/2006 | Monfre et al. |
| 6,800,988 B1 | 10/2004 | Ribak | | 6,999,810 B2 | 2/2006 | Berner et al. |
| 6,801,137 B2 | 10/2004 | Eggers | | 7,002,468 B2 | 2/2006 | Eveland et al. |
| 6,802,811 B1 | 10/2004 | Slepian | | 7,003,335 B2 | 2/2006 | Briancon |
| 6,804,558 B2 | 10/2004 | Haller et al. | | 7,003,336 B2 | 2/2006 | Holker et al. |
| 6,804,559 B1 | 10/2004 | Kraus et al. | | 7,005,986 B2 | 2/2006 | Parks, III et al. |
| 6,806,808 B1 | 10/2004 | Watters et al. | | 7,006,881 B1 | 2/2006 | Hoffberg et al. |
| 6,809,653 B1 | 10/2004 | Mann et al. | | 7,009,511 B2 | 3/2006 | Mazar et al. |
| 6,809,700 B2 | 10/2004 | Benedict et al. | | 7,009,517 B2 | 3/2006 | Wood |
| 6,809,701 B2 | 10/2004 | Amundson et al. | | 7,012,504 B2 | 3/2006 | Tuttle |
| 6,810,290 B2 | 10/2004 | Lebel et al. | | 7,014,111 B2 | 3/2006 | Bui et al. |
| 6,811,533 B2 | 11/2004 | Lebel et al. | | 7,015,826 B1 | 3/2006 | Chan et al. |
| 6,811,534 B2 | 11/2004 | Bowman, IV et al. | | 7,018,360 B2 | 3/2006 | Flaherty et al. |
| 6,813,519 B2 | 11/2004 | Lebel et al. | | 7,018,735 B2 | 3/2006 | Heller |
| 6,814,844 B2 | 11/2004 | Bhullar et al. | | 7,020,508 B2 | 3/2006 | Stivoric et al. |
| 6,820,012 B2 | 11/2004 | Sunshine | | 7,022,072 B2 | 4/2006 | Fox et al. |
| 6,825,767 B2 | 11/2004 | Humbard | | 7,024,236 B2 | 4/2006 | Ford et al. |
| 6,827,702 B2 | 12/2004 | Lebel et al. | | 7,024,245 B2 | 4/2006 | Lebel et al. |
| 6,830,558 B2 | 12/2004 | Flaherty et al. | | 7,024,248 B2 | 4/2006 | Penner et al. |
| 6,833,790 B2 | 12/2004 | Mejia et al. | | 7,024,249 B2 | 4/2006 | Weisner et al. |
| 6,833,987 B1 | 12/2004 | O'Phelan | | 7,024,369 B1 | 4/2006 | Brown et al. |
| 6,837,095 B2 | 1/2005 | Sunshine et al. | | 7,026,936 B2 | 4/2006 | Roesner |
| 6,838,988 B2 | 1/2005 | Lennartz et al. | | 7,026,939 B2 | 4/2006 | Letkomiller et al. |
| 6,842,478 B1 | 1/2005 | Ogino | | 7,027,862 B2 | 4/2006 | Dahl et al. |
| 6,847,912 B2 | 1/2005 | Forster | | 7,027,871 B2 | 4/2006 | Burnes et al. |
| 6,850,790 B2 | 2/2005 | Berner et al. | | 7,029,444 B2 | 4/2006 | Shin et al. |
| 6,853,087 B2 | 2/2005 | Neuhaus et al. | | 7,029,455 B2 | 4/2006 | Flaherty |
| 6,853,347 B2 | 2/2005 | Forster et al. | | 7,034,660 B2 | 4/2006 | Watters et al. |
| 6,862,465 B2 | 3/2005 | Shults et al. | | 7,035,170 B2 | 4/2006 | Narayanaswami et al. |
| 6,866,629 B2 | 3/2005 | Bardy | | 7,040,139 B2 | 5/2006 | Sunshine |
| 6,872,200 B2 | 3/2005 | Mann et al. | | 7,041,468 B2 | 5/2006 | Drucker et al. |
| 6,873,268 B2 | 3/2005 | Lebel et al. | | 7,043,305 B2 | 5/2006 | KenKnight et al. |
| 6,878,111 B2 | 4/2005 | Kenknight et al. | | 7,044,911 B2 | 5/2006 | Drinan et al. |
| 6,878,112 B2 | 4/2005 | Linberg et al. | | 7,045,046 B2 | 5/2006 | Chambers et al. |
| 6,880,085 B1 | 4/2005 | Balczewski et al. | | 7,047,076 B1 | 5/2006 | Li et al. |
| 6,882,940 B2 | 4/2005 | Potts et al. | | 7,049,962 B2 | 5/2006 | Atherton et al. |
| 6,885,883 B2 | 4/2005 | Parris et al. | | 7,052,178 B2 | 5/2006 | Urbas et al. |
| 6,885,894 B2 | 4/2005 | Stessman | | 7,052,251 B2 | 5/2006 | Nason et al. |
| 6,887,201 B2 | 5/2005 | Bardy | | 7,053,771 B2 | 5/2006 | Hussmann |
| 6,889,086 B2 | 5/2005 | Mass et al. | | 7,058,453 B2 | 6/2006 | Nelson et al. |
| 6,889,165 B2 | 5/2005 | Lind et al. | | 7,060,030 B2 | 6/2006 | Von Arx et al. |
| 6,889,833 B2 | 5/2005 | Seiler et al. | | 7,060,031 B2 | 6/2006 | Webb et al. |
| 6,891,474 B1 | 5/2005 | Fletcher | | 7,061,061 B2 | 6/2006 | Goodman et al. |
| 6,893,395 B1 | 5/2005 | Kraus et al. | | 7,065,409 B2 | 6/2006 | Mazar |
| 6,893,397 B2 | 5/2005 | Bardy | | 7,069,086 B2 | 6/2006 | Von Arx |
| 6,895,263 B2 | 5/2005 | Shin et al. | | 7,070,562 B2 | 7/2006 | Bardy |
| 6,895,281 B1 | 5/2005 | Amundson et al. | | 7,072,718 B2 | 7/2006 | Von Arx et al. |
| 6,897,788 B2 | 5/2005 | Khair et al. | | 7,073,246 B2 | 7/2006 | Bhullar et al. |
| 6,898,150 B2 | 5/2005 | Hahn et al. | | 7,074,307 B2 | 7/2006 | Simpson et al. |
| 6,903,704 B2 | 6/2005 | Forster et al. | | 7,075,436 B2 | 7/2006 | Shanks et al. |
| 6,903,723 B1 | 6/2005 | Forest | | 7,079,034 B2 | 7/2006 | Stilp |
| 6,906,624 B2 | 6/2005 | McClelland et al. | | 7,081,195 B2 | 7/2006 | Simpson et al. |
| 6,910,084 B2 | 6/2005 | Augustijn et al. | | 7,082,334 B2 | 7/2006 | Boute et al. |
| 6,916,159 B2 | 7/2005 | Rush et al. | | 7,088,226 B2 | 8/2006 | McClelland et al. |
| 6,931,284 B2 | 8/2005 | Engmark et al. | | 7,088,233 B2 | 8/2006 | Menard |
| 6,931,327 B2 | 8/2005 | Goode, Jr. et al. | | 7,089,099 B2 | 8/2006 | Shostak et al. |
| 6,934,267 B1 | 8/2005 | Mannerstrale | | 7,093,345 B2 | 8/2006 | Forster et al. |
| 6,934,572 B2 | 8/2005 | Schulman et al. | | 7,096,068 B2 | 8/2006 | Mass et al. |
| 6,940,403 B2 | 9/2005 | Kail, IV | | 7,098,850 B2 | 8/2006 | King et al. |
| 6,940,408 B2 | 9/2005 | Ferguson et al. | | 7,099,382 B2 | 8/2006 | Aronson et al. |
| 6,941,163 B2 | 9/2005 | Ford et al. | | 7,102,520 B2 | 9/2006 | Liu et al. |
| 6,942,518 B2 | 9/2005 | Liamos et al. | | 7,102,541 B2 | 9/2006 | Rosenberg |
| 6,942,615 B2 | 9/2005 | Suzuki et al. | | 7,103,388 B2 | 9/2006 | Scott |
| 6,946,989 B2 | 9/2005 | Vavik | | 7,103,413 B2 | 9/2006 | Swanson et al. |
| 6,950,009 B1 | 9/2005 | Nysen | | 7,104,955 B2 | 9/2006 | Bardy |
| 6,952,560 B2 | 10/2005 | Feibig et al. | | 7,107,099 B1 | 9/2006 | O'Phelan et al. |
| 6,957,107 B2 | 10/2005 | Rogers et al. | | 7,108,778 B2 | 9/2006 | Simpson et al. |
| 6,958,705 B2 | 10/2005 | Lebel et al. | | 7,109,868 B2 | 9/2006 | Yoakum |
| 6,960,167 B2 | 11/2005 | Bardy | | 7,109,878 B2 | 9/2006 | Mann et al. |
| 6,960,192 B1 | 11/2005 | Flaherty et al. | | 7,110,803 B2 | 9/2006 | Shults et al. |
| 6,961,000 B2 | 11/2005 | Chung | | 7,110,823 B2 | 9/2006 | Whitehurst et al. |
| 6,974,437 B2 | 12/2005 | Lebel et al. | | 7,110,824 B2 | 9/2006 | Amundson et al. |
| 6,978,182 B2 | 12/2005 | Mazar et al. | | 7,124,222 B2 | 10/2006 | Bar-Or |
| 6,985,773 B2 | 1/2006 | Von Arx et al. | | 7,125,382 B2 | 10/2006 | Zhou et al. |
| 6,993,393 B2 | 1/2006 | Von Arx et al. | | 7,127,300 B2 | 10/2006 | Mazar et al. |
| 6,995,685 B2 | 2/2006 | Randall | | 7,132,659 B2 | 11/2006 | Starta et al. |
| 6,996,215 B2 | 2/2006 | MacConnell | | 7,134,996 B2 | 11/2006 | Bardy |

| Patent | Date | Inventor |
|---|---|---|
| 7,134,999 B2 | 11/2006 | Brauker et al. |
| 7,135,976 B2 | 11/2006 | Neff et al. |
| 7,136,689 B2 | 11/2006 | Shults et al. |
| 7,137,964 B2 | 11/2006 | Flaherty |
| 7,140,768 B2 | 11/2006 | Prabhakar |
| 7,142,114 B2 | 11/2006 | Crowley |
| 7,144,384 B2 | 12/2006 | Gorman et al. |
| 7,147,600 B2 | 12/2006 | Bardy |
| 7,149,581 B2 | 12/2006 | Goedeke |
| 7,149,773 B2 | 12/2006 | Haller et al. |
| 7,151,436 B2 | 12/2006 | Fischer et al. |
| 7,154,938 B2 | 12/2006 | Cumeralto et al. |
| 7,155,290 B2 | 12/2006 | Von Arx et al. |
| 7,156,809 B2 | 1/2007 | Quy |
| 7,161,484 B2 | 1/2007 | Tsoukalis |
| 7,163,511 B2 | 1/2007 | Conn et al. |
| 7,167,818 B2 | 1/2007 | Brown |
| 7,171,252 B1 | 1/2007 | Scarantino et al. |
| 7,171,274 B2 | 1/2007 | Starkweather et al. |
| 7,171,312 B2 | 1/2007 | Steinthal et al. |
| 7,171,849 B2 | 2/2007 | Kandler |
| 7,174,199 B2 | 2/2007 | Berner et al. |
| 7,177,699 B2 | 2/2007 | Fabian et al. |
| 7,181,505 B2 | 2/2007 | Haller et al. |
| 7,183,102 B2 | 2/2007 | Monfre et al. |
| 7,187,528 B2 | 3/2007 | Talbot et al. |
| 7,188,151 B2 | 3/2007 | Kumar et al. |
| 7,190,319 B2 | 3/2007 | Forster et al. |
| 7,191,013 B1 | 3/2007 | Miranda et al. |
| 7,192,450 B2 | 3/2007 | Brauker et al. |
| 7,193,563 B2 | 3/2007 | King et al. |
| 7,196,316 B2 | 3/2007 | Chan et al. |
| 7,201,035 B2 | 4/2007 | Sunshine |
| 7,203,545 B2 | 4/2007 | Schmitt et al. |
| 7,203,549 B2 | 4/2007 | Schommer et al. |
| 7,207,974 B2 | 4/2007 | Safabash et al. |
| 7,212,110 B1 | 5/2007 | Martin et al. |
| 7,212,122 B2 | 5/2007 | Gloekler et al. |
| 7,215,976 B2 | 5/2007 | Brideglall |
| 7,218,232 B2 | 5/2007 | DiSilvestro et al. |
| 7,218,969 B2 | 5/2007 | Vallapureddy et al. |
| 7,222,054 B2 | 5/2007 | Geva |
| 7,224,280 B2 | 5/2007 | Ferguson et al. |
| 7,225,032 B2 | 5/2007 | Schmeling et al. |
| 7,226,278 B2 | 6/2007 | Nason et al. |
| 7,226,978 B2 | 6/2007 | Tapsak et al. |
| 7,228,182 B2 | 6/2007 | Healy et al. |
| 7,231,251 B2 | 6/2007 | Yonce et al. |
| 7,235,050 B2 | 6/2007 | Schulman et al. |
| 7,236,742 B2 | 6/2007 | Hall et al. |
| 7,237,712 B2 | 7/2007 | DeRocco et al. |
| 7,239,916 B2 | 7/2007 | Thompson et al. |
| 7,240,833 B2 | 7/2007 | Zarembo |
| 7,241,266 B2 | 7/2007 | Zhou et al. |
| 7,242,259 B2 | 7/2007 | Heide et al. |
| 7,244,265 B2 | 7/2007 | Freeman et al. |
| 7,248,182 B2 | 7/2007 | Dudda et al. |
| 7,248,916 B2 | 7/2007 | Bardy |
| 7,248,972 B2 | 7/2007 | Sunshine |
| 7,252,636 B2 | 8/2007 | Brown |
| 7,256,695 B2 | 8/2007 | Hamel et al. |
| 7,257,447 B2 | 8/2007 | Cates et al. |
| 7,258,673 B2 | 8/2007 | Racchini et al. |
| 7,259,681 B2 | 8/2007 | Kwoen |
| 7,261,690 B2 | 8/2007 | Teller et al. |
| 7,263,406 B2 | 8/2007 | Toy et al. |
| 7,265,676 B2 | 9/2007 | Gordon et al. |
| 7,267,751 B2 | 9/2007 | Gelbart et al. |
| 7,270,633 B1 | 9/2007 | Goscha et al. |
| 7,271,677 B2 | 9/2007 | Troyk et al. |
| 7,272,445 B2 | 9/2007 | Phillips et al. |
| 7,276,029 B2 | 10/2007 | Goode, Jr. et al. |
| 7,277,478 B2 | 10/2007 | Friedrich et al. |
| 7,278,983 B2 | 10/2007 | Ireland et al. |
| 7,282,029 B1 | 10/2007 | Poulsen et al. |
| 7,285,090 B2 | 10/2007 | Stivoric et al. |
| 7,286,871 B2 | 10/2007 | Cohen |
| 7,287,699 B2 | 10/2007 | Liu |
| 7,289,761 B2 | 10/2007 | Mazar |
| 7,291,107 B2 | 11/2007 | Hellwig et al. |
| 7,292,139 B2 | 11/2007 | Mazar et al. |
| 7,292,828 B1 | 11/2007 | Liu et al. |
| 7,295,867 B2 | 11/2007 | Berner et al. |
| 7,297,110 B2 | 11/2007 | Goyal et al. |
| 7,297,112 B2 | 11/2007 | Zhou et al. |
| 7,298,272 B2 | 11/2007 | Larson et al. |
| 7,299,082 B2 | 11/2007 | Feldman et al. |
| 7,299,148 B2 | 11/2007 | Hunt et al. |
| 7,299,159 B2 | 11/2007 | Nanikashvili |
| 7,303,549 B2 | 12/2007 | Flaherty et al. |
| 7,307,521 B2 | 12/2007 | Funk et al. |
| 7,310,544 B2 | 12/2007 | Brister et al. |
| 7,311,665 B2 | 12/2007 | Hawthorne et al. |
| 7,312,710 B2 | 12/2007 | Humbard |
| 7,313,422 B2 | 12/2007 | White et al. |
| 7,313,441 B2 | 12/2007 | Mass et al. |
| 7,318,816 B2 | 1/2008 | Bobroff et al. |
| 7,319,396 B2 | 1/2008 | Homanfar et al. |
| 7,319,903 B2 | 1/2008 | Bange et al. |
| 7,324,850 B2 | 1/2008 | Persen et al. |
| 7,329,239 B2 | 2/2008 | Safabash et al. |
| 7,330,112 B1 | 2/2008 | Emigh et al. |
| 7,330,119 B2 | 2/2008 | Malone et al. |
| 7,330,120 B2 | 2/2008 | Malone et al. |
| 7,331,931 B2 | 2/2008 | Freeman et al. |
| 7,333,068 B2 | 2/2008 | Biddulph |
| 7,333,853 B2 | 2/2008 | Mazar et al. |
| 7,336,163 B2 | 2/2008 | Fujii |
| 7,342,508 B2 | 3/2008 | Morgan et al. |
| 7,343,265 B2 | 3/2008 | Andarawis et al. |
| 7,344,500 B2 | 3/2008 | Talbot et al. |
| 7,344,507 B2 | 3/2008 | Briggs et al. |
| 7,345,643 B2 | 3/2008 | Forster et al. |
| 7,347,819 B2 | 3/2008 | Lebel et al. |
| 7,354,420 B2 | 4/2008 | Steil et al. |
| 7,355,270 B2 | 4/2008 | Hasebe et al. |
| 7,355,841 B1 | 4/2008 | Schmidt et al. |
| 7,356,369 B2 | 4/2008 | Phillips et al. |
| 7,359,753 B2 | 4/2008 | Bange et al. |
| 7,363,087 B2 | 4/2008 | Nghiem et al. |
| 7,364,592 B2 | 4/2008 | Carr-Brendel et al. |
| 7,366,556 B2 | 4/2008 | Brister et al. |
| 7,373,142 B2 | 5/2008 | Scott |
| 7,373,713 B2 | 5/2008 | Forster et al. |
| 7,374,544 B2 | 5/2008 | Freeman et al. |
| 7,375,616 B2 | 5/2008 | Rowse et al. |
| 7,375,639 B2 | 5/2008 | Dixon et al. |
| 7,376,439 B2 | 5/2008 | White et al. |
| 7,378,955 B2 | 5/2008 | Mazar et al. |
| 7,378,973 B2 | 5/2008 | Dixon et al. |
| 7,379,765 B2 | 5/2008 | Petisce et al. |
| 7,384,396 B2 | 6/2008 | Samuels et al. |
| 7,384,397 B2 | 6/2008 | Zhang et al. |
| 7,386,937 B2 | 6/2008 | Bhullar et al. |
| 7,387,010 B2 | 6/2008 | Sunshine |
| 7,389,133 B1 | 6/2008 | Kotulla et al. |
| 7,389,146 B2 | 6/2008 | Hanson et al. |
| 7,392,090 B2 | 6/2008 | Sweeney et al. |
| 7,394,382 B2 | 7/2008 | Nitzan et al. |
| 7,394,438 B2 | 7/2008 | Forster et al. |
| 7,395,117 B2 | 7/2008 | Mazar et al. |
| 7,399,277 B2 | 7/2008 | Saidara et al. |
| 7,400,928 B2 | 7/2008 | Hatlestsad |
| 7,402,153 B2 | 7/2008 | Steil et al. |
| 7,406,349 B2 | 7/2008 | Seeberger et al. |
| 7,407,054 B2 | 8/2008 | Seiler et al. |
| 7,407,484 B2 | 8/2008 | Korman |
| 7,408,463 B2 | 8/2008 | Hammond et al. |
| 7,411,506 B2 | 8/2008 | Volpi et al. |
| 7,411,552 B2 | 8/2008 | King et al. |
| 7,414,589 B2 | 8/2008 | Forster et al. |
| 7,416,530 B2 | 8/2008 | Turner et al. |
| 7,418,296 B2 | 8/2008 | Freeberg |
| 7,419,573 B2 | 9/2008 | Gundel |
| 7,420,520 B2 | 9/2008 | Forster et al. |
| 7,424,318 B2 | 9/2008 | Brister et al. |
| 7,429,920 B2 | 9/2008 | Smythe et al. |
| 7,432,809 B2 | 10/2008 | Malacarne et al. |

| Patent | Date | Inventor |
|---|---|---|
| 7,432,825 B2 | 10/2008 | Chan et al. |
| 7,433,853 B2 | 10/2008 | Brockway et al. |
| 7,437,644 B2 | 10/2008 | Ginggen et al. |
| 7,440,805 B2 | 10/2008 | Holmquist et al. |
| 7,446,714 B2 | 11/2008 | Biddulph |
| 7,448,996 B2 | 11/2008 | Khanuja et al. |
| 7,450,986 B2 | 11/2008 | Nguyen et al. |
| 7,450,996 B2 | 11/2008 | MacDonald et al. |
| 7,457,669 B2 | 11/2008 | Katoozi et al. |
| 7,459,979 B2 | 12/2008 | Rotay et al. |
| 7,460,898 B2 | 12/2008 | Brister et al. |
| 7,463,142 B2 | 12/2008 | Lindsay |
| 7,467,003 B2 | 12/2008 | Brister et al. |
| 7,468,032 B2 | 12/2008 | Stahmann et al. |
| 7,469,161 B1 | 12/2008 | Gandhi et al. |
| 7,469,838 B2 | 12/2008 | Brooks et al. |
| 7,471,972 B2 | 12/2008 | Rhodes et al. |
| 7,471,980 B2 | 12/2008 | Koshiol et al. |
| 7,471,986 B2 | 12/2008 | Hatlestad |
| 7,474,223 B2 | 1/2009 | Nycz et al. |
| 7,474,886 B2 | 1/2009 | Heller |
| 7,475,245 B1 | 1/2009 | Healy et al. |
| 7,476,827 B1 | 1/2009 | Bhullar et al. |
| 7,478,108 B2 | 1/2009 | Townsend et al. |
| 7,481,368 B2 | 1/2009 | Wang et al. |
| 7,483,752 B2 | 1/2009 | Von Arx et al. |
| 7,491,178 B2 | 2/2009 | Boecker et al. |
| 7,491,303 B2 | 2/2009 | Sakata et al. |
| 7,492,812 B2 | 2/2009 | Ninomiya et al. |
| 7,493,174 B2 | 2/2009 | Belalcazar et al. |
| 7,494,459 B2 | 2/2009 | Anstadt et al. |
| 7,494,465 B2 | 2/2009 | Brister et al. |
| 7,497,827 B2 | 3/2009 | Brister et al. |
| 7,498,948 B1 | 3/2009 | Gudeman et al. |
| 7,501,289 B2 | 3/2009 | Kubo et al. |
| 7,504,951 B2 | 3/2009 | Phipps et al. |
| 7,516,450 B2 | 4/2009 | Ogura |
| 7,519,408 B2 | 4/2009 | Rasdal et al. |
| 7,519,424 B2 | 4/2009 | Dennis et al. |
| 7,519,430 B2 | 4/2009 | Von Arx et al. |
| 7,521,890 B2 | 4/2009 | Lee et al. |
| 7,522,040 B2 | 4/2009 | Passmore et al. |
| 7,525,426 B2 | 4/2009 | Edelstein et al. |
| 7,528,094 B2 | 5/2009 | Blaha et al. |
| 7,528,725 B2 | 5/2009 | Stewart |
| 7,535,360 B2 | 5/2009 | Barink et al. |
| 7,536,206 B2 | 5/2009 | Hardy et al. |
| 7,539,488 B2 | 5/2009 | Friedman |
| 7,539,541 B2 | 5/2009 | Quiles et al. |
| 7,542,878 B2 | 6/2009 | Nanikashvili |
| 7,545,272 B2 | 6/2009 | Goodnow et al. |
| 7,550,310 B2 | 6/2009 | Goodman et al. |
| 7,550,978 B2 | 6/2009 | Joy et al. |
| 7,553,280 B2 | 6/2009 | Lesho |
| 7,553,281 B2 | 6/2009 | Hellwig et al. |
| 7,554,438 B2 | 6/2009 | Mazar et al. |
| 7,555,436 B2 | 6/2009 | Brown |
| 7,561,855 B2 | 7/2009 | Hofmeister et al. |
| 7,561,912 B2 | 7/2009 | Schatz et al. |
| 7,561,921 B2 | 7/2009 | Phillips et al. |
| 7,565,197 B2 | 7/2009 | Haubrich et al. |
| 7,567,758 B2 | 7/2009 | Aronson et al. |
| 7,569,030 B2 | 8/2009 | Lebel et al. |
| 7,569,050 B2 | 8/2009 | Moberg et al. |
| 7,571,008 B2 | 8/2009 | Dinsmoor et al. |
| 7,573,389 B2 | 8/2009 | Kiyohara |
| 7,574,266 B2 | 8/2009 | Dudding et al. |
| 7,578,432 B2 | 8/2009 | Libin et al. |
| 7,583,990 B2 | 9/2009 | Goode, Jr. et al. |
| 7,586,416 B2 | 9/2009 | Ariyoshi et al. |
| 7,591,801 B2 | 9/2009 | Brauker et al. |
| 7,595,723 B2 | 9/2009 | Heitzmann et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,610,094 B2 | 10/2009 | Stahmann et al. |
| 7,612,652 B2 | 11/2009 | Stewart et al. |
| 7,613,491 B2 | 11/2009 | Boock et al. |
| 7,613,497 B2 | 11/2009 | Govari et al. |
| 7,613,521 B2 | 11/2009 | Mass et al. |
| 7,615,007 B2 | 11/2009 | Shults et al. |
| 7,616,110 B2 | 11/2009 | Crump et al. |
| 7,616,117 B2 | 11/2009 | Streeb |
| 7,616,992 B2 | 11/2009 | Dennis et al. |
| 7,620,437 B2 | 11/2009 | Reggiardo |
| 7,623,234 B2 | 11/2009 | Puzey |
| 7,623,834 B2 | 11/2009 | Forster |
| 7,624,028 B1 | 11/2009 | Brown |
| 7,629,531 B2 | 12/2009 | Stark |
| 7,632,228 B2 | 12/2009 | Brauker et al. |
| 7,632,672 B2 | 12/2009 | Pamidi et al. |
| 7,633,378 B2 | 12/2009 | Rodgers et al. |
| 7,637,868 B2 | 12/2009 | Saint et al. |
| 7,640,048 B2 | 12/2009 | Dobbles et al. |
| 7,641,619 B2 | 1/2010 | Penner |
| 7,641,649 B2 | 1/2010 | Moberg et al. |
| 7,645,233 B2 | 1/2010 | Tulkki et al. |
| 7,647,237 B2 | 1/2010 | Malave et al. |
| 7,648,468 B2 | 1/2010 | Boecker et al. |
| 7,650,187 B2 | 1/2010 | Gruber et al. |
| 7,651,489 B2 | 1/2010 | Estes et al. |
| 7,651,596 B2 | 1/2010 | Petisce et al. |
| 7,654,129 B2 | 2/2010 | Bonne et al. |
| 7,654,956 B2 | 2/2010 | Brister et al. |
| 7,656,931 B2 | 2/2010 | Smith et al. |
| 7,657,295 B2 | 2/2010 | Coakley et al. |
| 7,657,297 B2 | 2/2010 | Simpson et al. |
| 7,659,826 B2 | 2/2010 | Humbard |
| 7,664,553 B2 | 2/2010 | Roberts |
| 7,667,575 B2 | 2/2010 | Husak et al. |
| 7,668,596 B2 | 2/2010 | Von Arx et al. |
| 7,670,288 B2 | 3/2010 | Sher |
| 7,678,071 B2 | 3/2010 | Lebel et al. |
| 7,679,162 B2 | 3/2010 | Dupuis et al. |
| 7,686,762 B1 | 3/2010 | Najafi et al. |
| 7,686,787 B2 | 3/2010 | Moberg et al. |
| 7,689,437 B1 | 3/2010 | Teller et al. |
| 7,689,440 B2 | 3/2010 | Brown |
| 7,697,492 B2 | 4/2010 | Petite |
| 7,711,402 B2 | 5/2010 | Shults et al. |
| 7,713,574 B2 | 5/2010 | Brister et al. |
| 7,715,893 B2 | 5/2010 | Kamath et al. |
| 7,729,766 B2 | 6/2010 | Toy et al. |
| 7,774,145 B2 | 8/2010 | Brauker et al. |
| 7,778,680 B2 | 8/2010 | Goode, Jr. et al. |
| 7,779,183 B2 | 8/2010 | Koehler et al. |
| 7,782,192 B2 | 8/2010 | Jeckelmann et al. |
| 7,783,333 B2 | 8/2010 | Brister et al. |
| 2001/0013006 A1 | 8/2001 | Brown |
| 2001/0025189 A1 | 9/2001 | Haueter et al. |
| 2001/0033233 A1 | 10/2001 | Jentsch et al. |
| 2001/0037056 A1 | 11/2001 | Nunome |
| 2001/0039372 A1 | 11/2001 | Yasushi et al. |
| 2001/0044588 A1 | 11/2001 | Mault |
| 2001/0047125 A1 | 11/2001 | Quy |
| 2001/0047127 A1 | 11/2001 | New et al. |
| 2001/0047194 A1 | 11/2001 | Thompson et al. |
| 2001/0049471 A1 | 12/2001 | Suzuki et al. |
| 2002/0013538 A1 | 1/2002 | Teller |
| 2002/0019584 A1 | 2/2002 | Schulze et al. |
| 2002/0019748 A1 | 2/2002 | Brown |
| 2002/0031446 A1 | 3/2002 | Friedlander et al. |
| 2002/0040208 A1 | 4/2002 | Flaherty et al. |
| 2002/0042561 A1 | 4/2002 | Schulman et al. |
| 2002/0049374 A1 | 4/2002 | Abreu |
| 2002/0052539 A1 | 5/2002 | Haller et al. |
| 2002/0065453 A1 | 5/2002 | Lesho et al. |
| 2002/0067256 A1 | 6/2002 | Kail, IV |
| 2002/0070857 A1 | 6/2002 | Brooks et al. |
| 2002/0072733 A1 | 6/2002 | Flaherty |
| 2002/0072784 A1 | 6/2002 | Sheppard et al. |
| 2002/0080938 A1 | 6/2002 | Alexander, III et al. |
| 2002/0082665 A1 | 6/2002 | Haller et al. |
| 2002/0087146 A1 | 7/2002 | Schu et al. |
| 2002/0095196 A1 | 7/2002 | Linberg |
| 2002/0099282 A1 | 7/2002 | Knobbe et al. |
| 2002/0103425 A1 | 8/2002 | Mault |
| 2002/0107476 A1 | 8/2002 | Mann et al. |

| Pub. No. | Date | Inventor |
|---|---|---|
| 2002/0115920 A1 | 8/2002 | Rich et al. |
| 2002/0128594 A1 | 9/2002 | Das et al. |
| 2002/0129633 A1 | 9/2002 | Joki et al. |
| 2002/0132585 A1 | 9/2002 | Palermo et al. |
| 2002/0149416 A1 | 10/2002 | Bandy et al. |
| 2002/0151770 A1 | 10/2002 | Noll, III et al. |
| 2002/0151816 A1 | 10/2002 | Rich et al. |
| 2002/0167405 A1 | 11/2002 | Shanks et al. |
| 2002/0183800 A1 | 12/2002 | Schmidt et al. |
| 2002/0188214 A1 | 12/2002 | Misczynski et al. |
| 2003/0014082 A1 | 1/2003 | Schu et al. |
| 2003/0014090 A1 | 1/2003 | Abrahamson |
| 2003/0014091 A1 | 1/2003 | Rastegar et al. |
| 2003/0020595 A1 | 1/2003 | Wacyk |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0034715 A1 | 2/2003 | Burns et al. |
| 2003/0052788 A1 | 3/2003 | Kwong Tai Chung |
| 2003/0052821 A1 | 3/2003 | Holt |
| 2003/0063524 A1* | 4/2003 | Niemiec et al. ............... 368/10 |
| 2003/0065308 A1 | 4/2003 | Lebel et al. |
| 2003/0069489 A1 | 4/2003 | Abreu |
| 2003/0076263 A1 | 4/2003 | Hassan-Zade et al. |
| 2003/0078481 A1 | 4/2003 | McIvor et al. |
| 2003/0085684 A1 | 5/2003 | Tsukamoto et al. |
| 2003/0088238 A1 | 5/2003 | Poulsen et al. |
| 2003/0088290 A1 | 5/2003 | Spinelli et al. |
| 2003/0093301 A1 | 5/2003 | Chesney et al. |
| 2003/0097092 A1 | 5/2003 | Flaherty |
| 2003/0100040 A1 | 5/2003 | Bonnecaze et al. |
| 2003/0107487 A1 | 6/2003 | Korman et al. |
| 2003/0114897 A1 | 6/2003 | Von Arx et al. |
| 2003/0123389 A1 | 7/2003 | Russell et al. |
| 2003/0128119 A1 | 7/2003 | Lake |
| 2003/0128121 A1 | 7/2003 | Nee |
| 2003/0130567 A1 | 7/2003 | Mault et al. |
| 2003/0130616 A1 | 7/2003 | Steil et al. |
| 2003/0135125 A1 | 7/2003 | Lu et al. |
| 2003/0136417 A1 | 7/2003 | Fonseca et al. |
| 2003/0139677 A1 | 7/2003 | Fonseca et al. |
| 2003/0141981 A1 | 7/2003 | Bui et al. |
| 2003/0143746 A1 | 7/2003 | Sage |
| 2003/0144579 A1 | 7/2003 | Buss |
| 2003/0144711 A1 | 7/2003 | Pless et al. |
| 2003/0153821 A1 | 8/2003 | Berner et al. |
| 2003/0153832 A1 | 8/2003 | Zumeris et al. |
| 2003/0176785 A1 | 9/2003 | Buckman et al. |
| 2003/0176807 A1 | 9/2003 | Goetz et al. |
| 2003/0176933 A1 | 9/2003 | Lebel et al. |
| 2003/0181798 A1 | 9/2003 | Al Ali |
| 2003/0181851 A1 | 9/2003 | Mann et al. |
| 2003/0194205 A1 | 10/2003 | Suzuki et al. |
| 2003/0195398 A1 | 10/2003 | Suzuki et al. |
| 2003/0195578 A1 | 10/2003 | Perron et al. |
| 2003/0199778 A1 | 10/2003 | Mickle et al. |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2003/0216793 A1 | 11/2003 | Karlsson et al. |
| 2003/0217966 A1 | 11/2003 | Tapsak et al. |
| 2003/0224729 A1 | 12/2003 | Arnold |
| 2003/0225324 A1 | 12/2003 | Anderson et al. |
| 2003/0225362 A1 | 12/2003 | Currie et al. |
| 2003/0229514 A2 | 12/2003 | Brown |
| 2003/0233257 A1 | 12/2003 | Matian et al. |
| 2004/0003073 A1 | 1/2004 | Krzyzanowski et al. |
| 2004/0010425 A1 | 1/2004 | Wilkes et al. |
| 2004/0011671 A1 | 1/2004 | Shults et al. |
| 2004/0012620 A1 | 1/2004 | Buhler et al. |
| 2004/0012701 A1 | 1/2004 | Nagai et al. |
| 2004/0015102 A1 | 1/2004 | Cummings et al. |
| 2004/0016488 A1 | 1/2004 | Benedict et al. |
| 2004/0032226 A1 | 2/2004 | Lys |
| 2004/0034289 A1 | 2/2004 | Teller et al. |
| 2004/0034295 A1 | 2/2004 | Salganicoff |
| 2004/0045879 A1 | 3/2004 | Shults et al. |
| 2004/0049246 A1 | 3/2004 | Almendinger et al. |
| 2004/0053295 A1 | 3/2004 | McKinnon et al. |
| 2004/0054263 A1 | 3/2004 | Moerman et al. |
| 2004/0063167 A1 | 4/2004 | Kaastrup et al. |
| 2004/0068230 A1 | 4/2004 | Estes et al. |
| 2004/0073095 A1 | 4/2004 | Causey, III et al. |
| 2004/0073453 A1 | 4/2004 | Nenov et al. |
| 2004/0076119 A1 | 4/2004 | Aronson et al. |
| 2004/0077383 A1 | 4/2004 | Lappetelainen et al. |
| 2004/0077995 A1 | 4/2004 | Ferek-Petric et al. |
| 2004/0080299 A1 | 4/2004 | Forster et al. |
| 2004/0082098 A1 | 4/2004 | Schmid |
| 2004/0100376 A1 | 5/2004 | Lye et al. |
| 2004/0102815 A1 | 5/2004 | Balczewski et al. |
| 2004/0106376 A1 | 6/2004 | Forster |
| 2004/0108225 A1 | 6/2004 | Friedlander et al. |
| 2004/0113771 A1 | 6/2004 | Ozaki et al. |
| 2004/0118704 A1 | 6/2004 | Wang et al. |
| 2004/0120848 A1 | 6/2004 | Teodorczyk |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122353 A1 | 6/2004 | Shahmirian et al. |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2004/0127774 A1 | 7/2004 | Moore et al. |
| 2004/0133081 A1 | 7/2004 | Teller et al. |
| 2004/0133086 A1 | 7/2004 | Ciurczak et al. |
| 2004/0133455 A1 | 7/2004 | McMahon |
| 2004/0135684 A1 | 7/2004 | Steinthal et al. |
| 2004/0137547 A1 | 7/2004 | Shah et al. |
| 2004/0139044 A1 | 7/2004 | Rehwald |
| 2004/0140898 A1 | 7/2004 | Reeves |
| 2004/0140904 A1 | 7/2004 | Bertness |
| 2004/0142705 A1 | 7/2004 | Casebolt et al. |
| 2004/0143306 A1 | 7/2004 | Conley et al. |
| 2004/0152961 A1 | 8/2004 | Carlson et al. |
| 2004/0155079 A1 | 8/2004 | Shetler et al. |
| 2004/0160322 A1 | 8/2004 | Stilp |
| 2004/0162473 A1 | 8/2004 | Sohrab |
| 2004/0172016 A1 | 9/2004 | Bek et al. |
| 2004/0172222 A1 | 9/2004 | Simpson et al. |
| 2004/0172301 A1 | 9/2004 | Mihai et al. |
| 2004/0172302 A1 | 9/2004 | Martucci et al. |
| 2004/0174258 A1 | 9/2004 | Edelstein et al. |
| 2004/0176667 A1 | 9/2004 | Mihai et al. |
| 2004/0176822 A1 | 9/2004 | Thompson et al. |
| 2004/0186362 A1 | 9/2004 | Brauker et al. |
| 2004/0199059 A1 | 10/2004 | Brauker et al. |
| 2004/0199212 A1 | 10/2004 | Fischell et al. |
| 2004/0199220 A1 | 10/2004 | Cantlon |
| 2004/0203381 A1 | 10/2004 | Cahn et al. |
| 2004/0204744 A1 | 10/2004 | Penner et al. |
| 2004/0211666 A1 | 10/2004 | Pamidi et al. |
| 2004/0212504 A1 | 10/2004 | Forcier et al. |
| 2004/0215269 A1 | 10/2004 | Burnes et al. |
| 2004/0223876 A1 | 11/2004 | Kirollos et al. |
| 2004/0233043 A1 | 11/2004 | Yazawa et al. |
| 2004/0233971 A1 | 11/2004 | Meads et al. |
| 2004/0248315 A1 | 12/2004 | Klein et al. |
| 2004/0249999 A1 | 12/2004 | Connolly et al. |
| 2004/0254434 A1 | 12/2004 | Goodnow et al. |
| 2004/0260233 A1 | 12/2004 | Garibotto et al. |
| 2004/0266480 A1 | 12/2004 | Hjelt et al. |
| 2004/0267501 A1 | 12/2004 | Freed et al. |
| 2005/0003470 A1 | 1/2005 | Nelson et al. |
| 2005/0004439 A1 | 1/2005 | Shin et al. |
| 2005/0010269 A1 | 1/2005 | Lebel et al. |
| 2005/0012596 A1 | 1/2005 | Wennrich et al. |
| 2005/0023137 A1 | 2/2005 | Bhullar et al. |
| 2005/0024187 A1 | 2/2005 | Kranz et al. |
| 2005/0026643 A1 | 2/2005 | White et al. |
| 2005/0027175 A1 | 2/2005 | Yang |
| 2005/0027180 A1 | 2/2005 | Goode, Jr. et al. |
| 2005/0027182 A1 | 2/2005 | Siddiqui et al. |
| 2005/0031689 A1 | 2/2005 | Shults et al. |
| 2005/0032511 A1 | 2/2005 | Malone et al. |
| 2005/0033127 A1 | 2/2005 | Ciurczak |

| | | | | | |
|---|---|---|---|---|---|
| 2005/0033148 A1 | 2/2005 | Haueter et al. | 2005/0212689 A1 | 9/2005 | Randall |
| 2005/0033385 A1 | 2/2005 | Peterson et al. | 2005/0215982 A1 | 9/2005 | Malave et al. |
| 2005/0038331 A1 | 2/2005 | Silaski et al. | 2005/0222645 A1 | 10/2005 | Malave et al. |
| 2005/0038680 A1 | 2/2005 | McMahon | 2005/0225437 A1 | 10/2005 | Shiotsu et al. |
| 2005/0043598 A1 | 2/2005 | Goode, Jr. et al. | 2005/0228247 A1 | 10/2005 | Scarantino et al. |
| 2005/0043674 A1 | 2/2005 | Blair et al. | 2005/0228313 A1 | 10/2005 | Kaler et al. |
| 2005/0049473 A1 | 3/2005 | Desai et al. | 2005/0237198 A1 | 10/2005 | Waldner et al. |
| 2005/0049501 A1 | 3/2005 | Conero et al. | 2005/0238507 A1 | 10/2005 | DiIanni et al. |
| 2005/0055242 A1 | 3/2005 | Bello et al. | 2005/0239156 A1 | 10/2005 | Drucker et al. |
| 2005/0055243 A1 | 3/2005 | Arndt et al. | 2005/0241026 A1 | 10/2005 | Esler et al. |
| 2005/0055244 A1 | 3/2005 | Mullan et al. | 2005/0242479 A1 | 11/2005 | Petisce et al. |
| 2005/0056552 A1 | 3/2005 | Simpson et al. | 2005/0245794 A1 | 11/2005 | Dinsmoor |
| 2005/0064528 A1 | 3/2005 | Kwon et al. | 2005/0245795 A1 | 11/2005 | Goode, Jr. et al. |
| 2005/0065464 A1 | 3/2005 | Talbot et al. | 2005/0245799 A1 | 11/2005 | Brauker et al. |
| 2005/0065556 A1 | 3/2005 | Reghabi et al. | 2005/0245839 A1 | 11/2005 | Stivoric et al. |
| 2005/0068182 A1 | 3/2005 | Dunlap et al. | 2005/0248438 A1 | 11/2005 | Hughes et al. |
| 2005/0068223 A1 | 3/2005 | Vavik | 2005/0250440 A1 | 11/2005 | Zhou et al. |
| 2005/0069925 A1 | 3/2005 | Ford et al. | 2005/0251227 A1 | 11/2005 | Khoo et al. |
| 2005/0075670 A1 | 4/2005 | Bengtsson | 2005/0267339 A1 | 12/2005 | Beckmann et al. |
| 2005/0075689 A1 | 4/2005 | Toy et al. | 2005/0267550 A1 | 12/2005 | Hess et al. |
| 2005/0075690 A1 | 4/2005 | Toy et al. | 2005/0267780 A1 | 12/2005 | Ray et al. |
| 2005/0075697 A1 | 4/2005 | Olson et al. | 2005/0272985 A1 | 12/2005 | Kotulla et al. |
| 2005/0080322 A1 | 4/2005 | Korman | 2005/0273080 A1 | 12/2005 | Paul |
| 2005/0080566 A1 | 4/2005 | Vock et al. | 2005/0277164 A1 | 12/2005 | Drucker et al. |
| 2005/0090607 A1 | 4/2005 | Tapsak et al. | 2005/0277872 A1 | 12/2005 | Colby, Jr. et al. |
| 2005/0090726 A1 | 4/2005 | Ackerman | 2005/0277873 A1 | 12/2005 | Stewart et al. |
| 2005/0090808 A1 | 4/2005 | Malave et al. | 2005/0281706 A1 | 12/2005 | Funke et al. |
| 2005/0092838 A1 | 5/2005 | Tsirline et al. | 2005/0288739 A1 | 12/2005 | Hassler, Jr. et al. |
| 2005/0096511 A1 | 5/2005 | Fox et al. | 2005/0288740 A1 | 12/2005 | Hassler, Jr. et al. |
| 2005/0096512 A1 | 5/2005 | Fox et al. | 2005/0288754 A1 | 12/2005 | Gray |
| 2005/0099269 A1 | 5/2005 | Diorio et al. | 2006/0001528 A1 | 1/2006 | Nitzan et al. |
| 2005/0101843 A1 | 5/2005 | Quinn et al. | 2006/0001538 A1 | 1/2006 | Kraft et al. |
| 2005/0101873 A1 | 5/2005 | Misczynski et al. | 2006/0001551 A1 | 1/2006 | Kraft et al. |
| 2005/0102167 A1 | 5/2005 | Kapoor | 2006/0004272 A1 | 1/2006 | Shah et al. |
| 2005/0107870 A1 | 5/2005 | Wang et al. | 2006/0004611 A1 | 1/2006 | Brown |
| 2005/0112169 A1 | 5/2005 | Brauker et al. | 2006/0007049 A1 | 1/2006 | Nitzan et al. |
| 2005/0113650 A1 | 5/2005 | Pacione et al. | 2006/0009817 A1 | 1/2006 | Tulkki |
| 2005/0113653 A1 | 5/2005 | Fox et al. | 2006/0009856 A1 | 1/2006 | Sherman et al. |
| 2005/0113886 A1 | 5/2005 | Fischell et al. | 2006/0010014 A1 | 1/2006 | Brown |
| 2005/0115832 A1 | 6/2005 | Simpson et al. | 2006/0010098 A1 | 1/2006 | Goodnow et al. |
| 2005/0116820 A1 | 6/2005 | Goldreich | 2006/0012464 A1 | 1/2006 | Nitzan et al. |
| 2005/0124874 A1 | 6/2005 | Ackerman | 2006/0015020 A1 | 1/2006 | Neale et al. |
| 2005/0124936 A1 | 6/2005 | Mogensen et al. | 2006/0016700 A1 | 1/2006 | Brister et al. |
| 2005/0134452 A1 | 6/2005 | Smith | 2006/0019327 A1 | 1/2006 | Brister et al. |
| 2005/0135288 A1 | 6/2005 | Al Ali | 2006/0019373 A1 | 1/2006 | Kahlman et al. |
| 2005/0137573 A1 | 6/2005 | McLaughlin | 2006/0020186 A1 | 1/2006 | Brister et al. |
| 2005/0143635 A1 | 6/2005 | Kamath et al. | 2006/0020187 A1 | 1/2006 | Brister et al. |
| 2005/0143636 A1 | 6/2005 | Zhang et al. | 2006/0020188 A1 | 1/2006 | Kamath et al. |
| 2005/0144042 A1 | 6/2005 | Joffe et al. | 2006/0020189 A1 | 1/2006 | Brister et al. |
| 2005/0148832 A1 | 7/2005 | Reghabi et al. | 2006/0020190 A1 | 1/2006 | Kamath et al. |
| 2005/0154271 A1 | 7/2005 | Rasdal et al. | 2006/0020191 A1 | 1/2006 | Brister et al. |
| 2005/0156039 A1 | 7/2005 | Carrender et al. | 2006/0020192 A1 | 1/2006 | Brister et al. |
| 2005/0159653 A1 | 7/2005 | Iijima et al. | 2006/0020290 A1 | 1/2006 | Degroot |
| 2005/0163293 A1 | 7/2005 | Hawthorne et al. | 2006/0020803 A1 | 1/2006 | O'Hagan et al. |
| 2005/0165317 A1 | 7/2005 | Turner et al. | 2006/0022801 A1 | 2/2006 | Husak et al. |
| 2005/0171503 A1 | 8/2005 | Van Den Berghe et al. | 2006/0022815 A1 | 2/2006 | Fischer et al. |
| 2005/0171512 A1 | 8/2005 | Flaherty | 2006/0030891 A1 | 2/2006 | Saltzstein et al. |
| 2005/0171513 A1 | 8/2005 | Mann et al. | 2006/0031094 A1 | 2/2006 | Cohen et al. |
| 2005/0175665 A1 | 8/2005 | Hunter et al. | 2006/0031102 A1 | 2/2006 | Teller et al. |
| 2005/0176136 A1 | 8/2005 | Burd et al. | 2006/0036139 A1 | 2/2006 | Brister et al. |
| 2005/0177398 A1 | 8/2005 | Watanabe et al. | 2006/0036140 A1 | 2/2006 | Brister et al. |
| 2005/0177615 A1 | 8/2005 | Hawthorne et al. | 2006/0036141 A1 | 2/2006 | Kamath et al. |
| 2005/0182306 A1 | 8/2005 | Sloan | 2006/0036142 A1 | 2/2006 | Brister et al. |
| 2005/0182307 A1 | 8/2005 | Currie et al. | 2006/0036143 A1 | 2/2006 | Brister et al. |
| 2005/0182308 A1 | 8/2005 | Bardy | 2006/0036144 A1 | 2/2006 | Brister et al. |
| 2005/0182358 A1 | 8/2005 | Veit et al. | 2006/0036145 A1 | 2/2006 | Brister et al. |
| 2005/0182366 A1 | 8/2005 | Vogt et al. | 2006/0040402 A1 | 2/2006 | Brauker et al. |
| 2005/0182389 A1 | 8/2005 | LaPorte et al. | 2006/0041229 A1 | 2/2006 | Garibotto et al. |
| 2005/0182451 A1 | 8/2005 | Griffin et al. | 2006/0047327 A1 | 3/2006 | Colvin et al. |
| 2005/0187482 A1 | 8/2005 | O'Brien et al. | 2006/0047538 A1 | 3/2006 | Condurso et al. |
| 2005/0187593 A1 | 8/2005 | Housworth et al. | 2006/0049714 A1 | 3/2006 | Liu et al. |
| 2005/0187720 A1 | 8/2005 | Goode, Jr. et al. | 2006/0049957 A1 | 3/2006 | Surgenor et al. |
| 2005/0192557 A1 | 9/2005 | Brauker et al. | 2006/0052084 A1 | 3/2006 | Diebold et al. |
| 2005/0192727 A1 | 9/2005 | Shostak et al. | 2006/0052679 A1 | 3/2006 | Kotulla et al. |
| 2005/0192837 A1 | 9/2005 | Fears et al. | 2006/0057960 A1 | 3/2006 | Tran |
| 2005/0195930 A1 | 9/2005 | Spital et al. | 2006/0058627 A1 | 3/2006 | Flaherty et al. |
| 2005/0197621 A1 | 9/2005 | Poulsen et al. | 2006/0064133 A1 | 3/2006 | Von Arx et al. |
| 2005/0203360 A1 | 9/2005 | Brauker et al. | 2006/0064134 A1 | 3/2006 | Mazar et al. |
| 2005/0203461 A1 | 9/2005 | Flaherty et al. | 2006/0064142 A1 | 3/2006 | Chavan et al. |

| Pub. No. | Date | Name |
|---|---|---|
| 2006/0064143 A1 | 3/2006 | Von Arx et al. |
| 2006/0074381 A1 | 4/2006 | Malave et al. |
| 2006/0074564 A1 | 4/2006 | Bartkowiak et al. |
| 2006/0075139 A1 | 4/2006 | Jungck |
| 2006/0076236 A1 | 4/2006 | Shah et al. |
| 2006/0076493 A1 | 4/2006 | Bluzer |
| 2006/0080152 A1 | 4/2006 | Brown |
| 2006/0085137 A1 | 4/2006 | Bartkowiak et al. |
| 2006/0089592 A1 | 4/2006 | Kadhiresan et al. |
| 2006/0091213 A1 | 5/2006 | Bui et al. |
| 2006/0094944 A1 | 5/2006 | Chuang |
| 2006/0094945 A1 | 5/2006 | Barman et al. |
| 2006/0094946 A1 | 5/2006 | Kellogg et al. |
| 2006/0106433 A1 | 5/2006 | Mazar et al. |
| 2006/0108974 A1 | 5/2006 | Castillo |
| 2006/0116667 A1 | 6/2006 | Hamel et al. |
| 2006/0116744 A1 | 6/2006 | Von Arx et al. |
| 2006/0122473 A1 | 6/2006 | Kill et al. |
| 2006/0122474 A1 | 6/2006 | Teller et al. |
| 2006/0122665 A1 | 6/2006 | Nghiem et al. |
| 2006/0122667 A1 | 6/2006 | Chavan et al. |
| 2006/0122863 A1 | 6/2006 | Gottesman et al. |
| 2006/0122864 A1 | 6/2006 | Gottesman et al. |
| 2006/0125492 A1 | 6/2006 | Andarawis et al. |
| 2006/0132317 A1 | 6/2006 | Letkomiller et al. |
| 2006/0136013 A1 | 6/2006 | Sherman |
| 2006/0142651 A1 | 6/2006 | Brister et al. |
| 2006/0142820 A1 | 6/2006 | Von Arx et al. |
| 2006/0145855 A1 | 7/2006 | Diorio et al. |
| 2006/0149597 A1 | 7/2006 | Powell et al. |
| 2006/0151342 A1 | 7/2006 | Yaguchi |
| 2006/0154642 A1 | 7/2006 | Scannell |
| 2006/0155180 A1 | 7/2006 | Brister et al. |
| 2006/0155336 A1 | 7/2006 | Heath |
| 2006/0157701 A1 | 7/2006 | Bauer et al. |
| 2006/0160204 A1 | 7/2006 | Hassanein et al. |
| 2006/0161224 A1 | 7/2006 | Samuelsson et al. |
| 2006/0161225 A1 | 7/2006 | Sormann et al. |
| 2006/0161460 A1 | 7/2006 | Smitherman et al. |
| 2006/0166629 A1 | 7/2006 | Reggiardo |
| 2006/0167518 A1 | 7/2006 | Gill et al. |
| 2006/0167519 A1 | 7/2006 | Gill et al. |
| 2006/0173259 A1 | 8/2006 | Flaherty et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0178024 A1 | 8/2006 | Overhultz et al. |
| 2006/0178633 A1 | 8/2006 | Garibotto et al. |
| 2006/0178914 A1 | 8/2006 | Brown |
| 2006/0183985 A1 | 8/2006 | Brister et al. |
| 2006/0186997 A1 | 8/2006 | Ostertag et al. |
| 2006/0189854 A1 | 8/2006 | Webb et al. |
| 2006/0189856 A1 | 8/2006 | Petisce et al. |
| 2006/0189863 A1 | 8/2006 | Peyser et al. |
| 2006/0195163 A1 | 8/2006 | KenKnight et al. |
| 2006/0199196 A1 | 9/2006 | O'Banion et al. |
| 2006/0200007 A1 | 9/2006 | Brockway et al. |
| 2006/0200019 A1 | 9/2006 | Petisce et al. |
| 2006/0200020 A1 | 9/2006 | Brister et al. |
| 2006/0200970 A1 | 9/2006 | Brister et al. |
| 2006/0201804 A1 | 9/2006 | Chambers et al. |
| 2006/0202805 A1 | 9/2006 | Schulman et al. |
| 2006/0202859 A1 | 9/2006 | Mastrototaro et al. |
| 2006/0208066 A1 | 9/2006 | Finn et al. |
| 2006/0212092 A1 | 9/2006 | Pless et al. |
| 2006/0214765 A1 | 9/2006 | Pitchers et al. |
| 2006/0214791 A1 | 9/2006 | Tethrake et al. |
| 2006/0219576 A1 | 10/2006 | Jina |
| 2006/0220881 A1 | 10/2006 | Al Ali et al. |
| 2006/0221902 A1 | 10/2006 | Chen et al. |
| 2006/0222566 A1 | 10/2006 | Brauker et al. |
| 2006/0224048 A1 | 10/2006 | Devaul et al. |
| 2006/0224051 A1 | 10/2006 | Teller et al. |
| 2006/0224141 A1 | 10/2006 | Rush et al. |
| 2006/0226992 A1 | 10/2006 | Al Ali |
| 2006/0235285 A1 | 10/2006 | Brister et al. |
| 2006/0235310 A1 | 10/2006 | O'Brien et al. |
| 2006/0235488 A1 | 10/2006 | Nycz et al. |
| 2006/0240549 A1 | 10/2006 | Minton |
| 2006/0241356 A1 | 10/2006 | Flaherty |
| 2006/0247710 A1 | 11/2006 | Goetz et al. |
| 2006/0247951 A1 | 11/2006 | Brown |
| 2006/0250251 A1 | 11/2006 | Stewart |
| 2006/0253005 A1 | 11/2006 | Drinan et al. |
| 2006/0253067 A1 | 11/2006 | Staib et al. |
| 2006/0253086 A1 | 11/2006 | Moberg et al. |
| 2006/0253303 A1 | 11/2006 | Brown |
| 2006/0257995 A1 | 11/2006 | Simpson et al. |
| 2006/0257996 A1 | 11/2006 | Simpson et al. |
| 2006/0258761 A1 | 11/2006 | Boock et al. |
| 2006/0258920 A1 | 11/2006 | Burd et al. |
| 2006/0258929 A1 | 11/2006 | Goode, Jr. et al. |
| 2006/0263763 A1 | 11/2006 | Simpson et al. |
| 2006/0264890 A1 | 11/2006 | Moberg et al. |
| 2006/0265181 A1 | 11/2006 | Stewart |
| 2006/0270382 A1 | 11/2006 | Lappetelainen et al. |
| 2006/0270922 A1 | 11/2006 | Brauker et al. |
| 2006/0270923 A1 | 11/2006 | Brauker et al. |
| 2006/0271112 A1 | 11/2006 | Martinson et al. |
| 2006/0274154 A1 | 12/2006 | Levien et al. |
| 2006/0274486 A1 | 12/2006 | Kim |
| 2006/0275857 A1 | 12/2006 | Kjaer et al. |
| 2006/0276972 A1 | 12/2006 | Light, II et al. |
| 2006/0279413 A1 | 12/2006 | Yeager |
| 2006/0281454 A1 | 12/2006 | Gray |
| 2006/0281980 A1 | 12/2006 | Randlov et al. |
| 2006/0281982 A1 | 12/2006 | Grata et al. |
| 2006/0281985 A1 | 12/2006 | Ward et al. |
| 2006/0282290 A1 | 12/2006 | Flaherty et al. |
| 2006/0285736 A1 | 12/2006 | Brown |
| 2006/0287691 A1 | 12/2006 | Drew |
| 2006/0287694 A1 | 12/2006 | Almendinger et al. |
| 2006/0287889 A1 | 12/2006 | Brown |
| 2006/0290496 A1 | 12/2006 | Peeters |
| 2006/0293571 A1 | 12/2006 | Bao et al. |
| 2007/0001856 A1 | 1/2007 | Diorio et al. |
| 2007/0002791 A1 | 1/2007 | Kasprzyk et al. |
| 2007/0004969 A1 | 1/2007 | Kong et al. |
| 2007/0005367 A1 | 1/2007 | DeJean et al. |
| 2007/0007975 A1 | 1/2007 | Hawkins et al. |
| 2007/0008141 A1 | 1/2007 | Sweetland |
| 2007/0010972 A1 | 1/2007 | Praskovsky et al. |
| 2007/0011028 A1 | 1/2007 | Sweeney |
| 2007/0013487 A1 | 1/2007 | Scholtz et al. |
| 2007/0015976 A1 | 1/2007 | Miesel et al. |
| 2007/0016381 A1 | 1/2007 | Kamath et al. |
| 2007/0016445 A1 | 1/2007 | Brown |
| 2007/0016446 A1 | 1/2007 | Brown |
| 2007/0016447 A1 | 1/2007 | Brown |
| 2007/0016448 A1 | 1/2007 | Brown |
| 2007/0024486 A1 | 2/2007 | McRae |
| 2007/0027367 A1 | 2/2007 | Oliver et al. |
| 2007/0027370 A1 | 2/2007 | Brauker et al. |
| 2007/0027381 A1 | 2/2007 | Stafford |
| 2007/0032706 A1 | 2/2007 | Kamath et al. |
| 2007/0032707 A1 | 2/2007 | Coakley et al. |
| 2007/0032738 A1 | 2/2007 | Flaherty et al. |
| 2007/0032989 A1 | 2/2007 | Hodges et al. |
| 2007/0038053 A1 | 2/2007 | Berner et al. |
| 2007/0038402 A1 | 2/2007 | Zhang |
| 2007/0038883 A1 | 2/2007 | Gerder et al. |
| 2007/0040449 A1 | 2/2007 | Spurlin et al. |
| 2007/0043416 A1 | 2/2007 | Callas et al. |
| 2007/0045756 A1 | 3/2007 | Chang et al. |
| 2007/0045902 A1 | 3/2007 | Brauker et al. |
| 2007/0049991 A1 | 3/2007 | Klostermann et al. |
| 2007/0053466 A1 | 3/2007 | Klostermann |
| 2007/0054651 A1 | 3/2007 | Farmer et al. |
| 2007/0055166 A1 | 3/2007 | Patil |
| 2007/0059196 A1 | 3/2007 | Brister et al. |
| 2007/0060800 A1 | 3/2007 | Drinan et al. |
| 2007/0060869 A1 | 3/2007 | Tolle et al. |
| 2007/0060870 A1 | 3/2007 | Tolle et al. |
| 2007/0060871 A1 | 3/2007 | Istoc et al. |
| 2007/0061167 A1 | 3/2007 | Brown |
| 2007/0063819 A1 | 3/2007 | Friedrich |
| 2007/0064516 A1 | 3/2007 | Briggs et al. |
| 2007/0066873 A1 | 3/2007 | Kamath et al. |

| | | | | | | |
|---|---|---|---|---|---|---|
| 2007/0067251 A1 | 3/2007 | Brown | | 2007/0197878 A1 | 8/2007 | Shklarski |
| 2007/0069860 A1 | 3/2007 | Akiyama et al. | | 2007/0197890 A1 | 8/2007 | Boock et al. |
| 2007/0073129 A1 | 3/2007 | Shah et al. | | 2007/0203481 A1 | 8/2007 | Gregg et al. |
| 2007/0078497 A1 | 4/2007 | Vandanacker | | 2007/0203547 A1 | 8/2007 | Costello et al. |
| 2007/0080223 A1 | 4/2007 | Japuntich | | 2007/0203966 A1 | 8/2007 | Brauker et al. |
| 2007/0081626 A1 | 4/2007 | Rule et al. | | 2007/0208243 A1 | 9/2007 | Gabriel et al. |
| 2007/0083090 A1 | 4/2007 | Sterling et al. | | 2007/0208244 A1 | 9/2007 | Brauker et al. |
| 2007/0083241 A1 | 4/2007 | Bardy | | 2007/0208245 A1 | 9/2007 | Brauker et al. |
| 2007/0083246 A1 | 4/2007 | Mazar et al. | | 2007/0208246 A1 | 9/2007 | Brauker et al. |
| 2007/0085677 A1 | 4/2007 | Neff et al. | | 2007/0210162 A1 | 9/2007 | Keen et al. |
| 2007/0088521 A1 | 4/2007 | Shmueli et al. | | 2007/0210923 A1 | 9/2007 | Butler et al. |
| 2007/0093786 A1 | 4/2007 | Goldsmith et al. | | 2007/0213603 A1 | 9/2007 | Brown |
| 2007/0093879 A1 | 4/2007 | Bek et al. | | 2007/0213608 A1 | 9/2007 | Brown |
| 2007/0096882 A1 | 5/2007 | Bandy et al. | | 2007/0213611 A1 | 9/2007 | Simpson et al. |
| 2007/0100222 A1 | 5/2007 | Mastrototaro et al. | | 2007/0216534 A1 | 9/2007 | Ferguson et al. |
| 2007/0100385 A1 | 5/2007 | Rawat et al. | | 2007/0219480 A1 | 9/2007 | Kamen et al. |
| 2007/0100396 A1 | 5/2007 | Freeberg | | 2007/0219597 A1 | 9/2007 | Kamen et al. |
| 2007/0100666 A1 | 5/2007 | Stivoric et al. | | 2007/0232879 A1 | 10/2007 | Brister et al. |
| 2007/0103110 A1 | 5/2007 | Sagoo | | 2007/0232880 A1 | 10/2007 | Siddiqui et al. |
| 2007/0106129 A1 | 5/2007 | Srivathsa et al. | | 2007/0235331 A1 | 10/2007 | Simpson et al. |
| 2007/0106133 A1 | 5/2007 | Satchwell et al. | | 2007/0237123 A1 | 10/2007 | Komoriya |
| 2007/0106172 A1 | 5/2007 | Abreu | | 2007/0237678 A1 | 10/2007 | Roesicke et al. |
| 2007/0110615 A1 | 5/2007 | Neel et al. | | 2007/0244383 A1 | 10/2007 | Talbot et al. |
| 2007/0118030 A1 | 5/2007 | Bruce et al. | | 2007/0247304 A1 | 10/2007 | Bonnefin et al. |
| 2007/0118054 A1 | 5/2007 | Pinhas et al. | | 2007/0249922 A1 | 10/2007 | Peyser et al. |
| 2007/0118188 A1 | 5/2007 | Von Arx et al. | | 2007/0255122 A1 | 11/2007 | Vol et al. |
| 2007/0118309 A1 | 5/2007 | Stewart | | 2007/0255123 A1 | 11/2007 | Cummings et al. |
| 2007/0118405 A1 | 5/2007 | Campbell et al. | | 2007/0255531 A1 | 11/2007 | Drew |
| 2007/0118588 A1 | 5/2007 | Brown | | 2007/0258395 A1 | 11/2007 | Jollota et al. |
| 2007/0120650 A1 | 5/2007 | Nagai et al. | | 2007/0264623 A1 | 11/2007 | Wang et al. |
| 2007/0120683 A1 | 5/2007 | Flippen et al. | | 2007/0265515 A1 | 11/2007 | Brister et al. |
| 2007/0123759 A1 | 5/2007 | Grata et al. | | 2007/0270672 A1 | 11/2007 | Hayter |
| 2007/0123946 A1 | 5/2007 | Masoud | | 2007/0273486 A1 | 11/2007 | Shiotsu et al. |
| 2007/0123949 A1 | 5/2007 | Dabney et al. | | 2007/0276201 A1 | 11/2007 | Lee et al. |
| 2007/0124278 A1 | 5/2007 | Lewis et al. | | 2007/0276294 A1 | 11/2007 | Gupta et al. |
| 2007/0129621 A1 | 6/2007 | Kellogg et al. | | 2007/0281657 A1 | 12/2007 | Brommer et al. |
| 2007/0135699 A1 | 6/2007 | Ward et al. | | 2007/0282398 A1 | 12/2007 | Healy et al. |
| 2007/0135865 A1 | 6/2007 | Schmitt et al. | | 2007/0285248 A1 | 12/2007 | Hamel et al. |
| 2007/0135866 A1 | 6/2007 | Baker et al. | | 2007/0287985 A1 | 12/2007 | Estes et al. |
| 2007/0136098 A1 | 6/2007 | Smythe et al. | | 2007/0288069 A1 | 12/2007 | Goscha et al. |
| 2007/0138253 A1 | 6/2007 | Libin et al. | | 2007/0293776 A1 | 12/2007 | Korzinov et al. |
| 2007/0142721 A1 | 6/2007 | Berner et al. | | 2007/0293843 A1 | 12/2007 | Ireland et al. |
| 2007/0142747 A1 | 6/2007 | Boecker et al. | | 2007/0299326 A1 | 12/2007 | Brown |
| 2007/0142767 A1 | 6/2007 | Frikart et al. | | 2008/0000779 A1 | 1/2008 | Wang et al. |
| 2007/0149875 A1 | 6/2007 | Ouyang et al. | | 2008/0009680 A1 | 1/2008 | Hassler, Jr. |
| 2007/0150019 A1 | 6/2007 | Youker et al. | | 2008/0009768 A1 | 1/2008 | Sohrab et al. |
| 2007/0150028 A1 | 6/2007 | Parkinson et al. | | 2008/0009824 A1 | 1/2008 | Moberg et al. |
| 2007/0152829 A1 | 7/2007 | Lindsay et al. | | 2008/0015422 A1 | 1/2008 | Wessel |
| 2007/0153705 A1 | 7/2007 | Rosar et al. | | 2008/0018432 A1 | 1/2008 | Volpi et al. |
| 2007/0156033 A1 | 7/2007 | Causey, III et al. | | 2008/0018433 A1 | 1/2008 | Pitt-Pladdy |
| 2007/0156094 A1 | 7/2007 | Safabash et al. | | 2008/0018468 A1 | 1/2008 | Volpi et al. |
| 2007/0156450 A1 | 7/2007 | Roehm et al. | | 2008/0018469 A1 | 1/2008 | Volpi et al. |
| 2007/0162089 A1 | 7/2007 | Mosesov | | 2008/0019422 A1 | 1/2008 | Smith et al. |
| 2007/0163472 A1 | 7/2007 | Muirhead | | 2008/0021511 A1 | 1/2008 | Scott et al. |
| 2007/0163880 A1 | 7/2007 | Woo et al. | | 2008/0021524 A1 | 1/2008 | Goscha et al. |
| 2007/0163894 A1 | 7/2007 | Wang et al. | | 2008/0021666 A1 | 1/2008 | Goode, Jr. et al. |
| 2007/0165020 A1 | 7/2007 | Haueter et al. | | 2008/0024294 A1 | 1/2008 | Mazar |
| 2007/0167850 A1 | 7/2007 | Russell et al. | | 2008/0028261 A1 | 1/2008 | Petruno et al. |
| 2007/0167874 A1 | 7/2007 | Freeman et al. | | 2008/0030369 A1 | 2/2008 | Mann et al. |
| 2007/0167994 A1 | 7/2007 | Shelton et al. | | 2008/0033254 A1 | 2/2008 | Kamath et al. |
| 2007/0167995 A1 | 7/2007 | Dudding et al. | | 2008/0033255 A1 | 2/2008 | Essenpreis et al. |
| 2007/0167997 A1 | 7/2007 | Forsberg et al. | | 2008/0033266 A1 | 2/2008 | Diab et al. |
| 2007/0168145 A1 | 7/2007 | Beyer et al. | | 2008/0033268 A1 | 2/2008 | Stafford |
| 2007/0168242 A1 | 7/2007 | Brown | | 2008/0033273 A1 | 2/2008 | Zhou et al. |
| 2007/0169080 A1 | 7/2007 | Friedman | | 2008/0033357 A1 | 2/2008 | Mann et al. |
| 2007/0169533 A1 | 7/2007 | Shah et al. | | 2008/0040449 A1 | 2/2008 | Grant et al. |
| 2007/0170887 A1 | 7/2007 | Harguth et al. | | 2008/0044829 A1 | 2/2008 | Yagi et al. |
| 2007/0171076 A1 | 7/2007 | Stevens et al. | | 2008/0045824 A1 | 2/2008 | Tapsak et al. |
| 2007/0173701 A1 | 7/2007 | Al Ali | | 2008/0045932 A1 | 2/2008 | Beau et al. |
| 2007/0173706 A1 | 7/2007 | Neinast et al. | | 2008/0052057 A1 | 2/2008 | Brown |
| 2007/0173709 A1 | 7/2007 | Petisce et al. | | 2008/0055111 A1 | 3/2008 | Morgan et al. |
| 2007/0173710 A1 | 7/2007 | Petisce et al. | | 2008/0058652 A1 | 3/2008 | Payne |
| 2007/0173712 A1 | 7/2007 | Shah et al. | | 2008/0058773 A1 | 3/2008 | John |
| 2007/0179352 A1 | 8/2007 | Randlov et al. | | 2008/0060955 A1 | 3/2008 | Goodnow |
| 2007/0179361 A1 | 8/2007 | Brown et al. | | 2008/0061961 A1 | 3/2008 | John |
| 2007/0179552 A1 | 8/2007 | Dennis et al. | | 2008/0064943 A1 | 3/2008 | Talbot et al. |
| 2007/0179734 A1 | 8/2007 | Chmiel et al. | | 2008/0065169 A1 | 3/2008 | Colliou et al. |
| 2007/0185550 A1 | 8/2007 | Vallapureddy et al. | | 2008/0065416 A1 | 3/2008 | Mazar et al. |
| 2007/0192869 A1 | 8/2007 | Garfinkle | | 2008/0071156 A1 | 3/2008 | Brister et al. |

| | | |
|---|---|---|
| 2008/0071314 A1 | 3/2008 | John |
| 2008/0071328 A1 | 3/2008 | Haubrich et al. |
| 2008/0077031 A1 | 3/2008 | Spinelli et al. |
| 2008/0083041 A1 | 4/2008 | Santini et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0091175 A1 | 4/2008 | Frikart et al. |
| 2008/0097170 A1 | 4/2008 | Brown |
| 2008/0097180 A1 | 4/2008 | Brown |
| 2008/0097553 A1 | 4/2008 | John |
| 2008/0103380 A1 | 5/2008 | Brown |
| 2008/0108888 A1 | 5/2008 | Brown |
| 2008/0108942 A1 | 5/2008 | Brister et al. |
| 2008/0109197 A1 | 5/2008 | Brown |
| 2008/0114228 A1 | 5/2008 | McCluskey et al. |
| 2008/0114412 A1 | 5/2008 | Bange et al. |
| 2008/0119705 A1 | 5/2008 | Patel et al. |
| 2008/0129550 A1 | 6/2008 | McRae |
| 2008/0133146 A1 | 6/2008 | Chang et al. |
| 2008/0136595 A1 | 6/2008 | Finkenzeller |
| 2008/0136700 A1 | 6/2008 | McRae |
| 2008/0139907 A1 | 6/2008 | Rao et al. |
| 2008/0145277 A1 | 6/2008 | Wohland |
| 2008/0147004 A1 | 6/2008 | Mann et al. |
| 2008/0147050 A1 | 6/2008 | Mann et al. |
| 2008/0154265 A1 | 6/2008 | Duda et al. |
| 2008/0154321 A1 | 6/2008 | Youker et al. |
| 2008/0156661 A1 | 7/2008 | Cooper et al. |
| 2008/0157928 A1 | 7/2008 | Butler et al. |
| 2008/0161654 A1 | 7/2008 | Teller et al. |
| 2008/0161655 A1 | 7/2008 | Teller et al. |
| 2008/0161715 A1 | 7/2008 | Stivoric et al. |
| 2008/0164975 A1 | 7/2008 | Butler et al. |
| 2008/0164977 A1 | 7/2008 | Butler et al. |
| 2008/0166747 A1 | 7/2008 | Hellinga et al. |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0167572 A1 | 7/2008 | Stivoric et al. |
| 2008/0167573 A1 | 7/2008 | Stivoric et al. |
| 2008/0167578 A1 | 7/2008 | Bryer et al. |
| 2008/0171918 A1 | 7/2008 | Teller et al. |
| 2008/0171919 A1 | 7/2008 | Stivoric et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0172043 A1 | 7/2008 | Sheppard et al. |
| 2008/0174494 A1 | 7/2008 | Suzuki et al. |
| 2008/0177154 A1 | 7/2008 | Hansen et al. |
| 2008/0177155 A1 | 7/2008 | Hansen et al. |
| 2008/0177158 A1 | 7/2008 | Teller et al. |
| 2008/0180249 A1 | 7/2008 | Butler et al. |
| 2008/0180304 A1 | 7/2008 | McRae |
| 2008/0180305 A1 | 7/2008 | McRae |
| 2008/0183051 A1 | 7/2008 | Teller et al. |
| 2008/0183052 A1 | 7/2008 | Teller et al. |
| 2008/0183061 A1 | 7/2008 | Goode et al. |
| 2008/0183399 A1 | 7/2008 | Goode et al. |
| 2008/0186137 A1 | 8/2008 | Butler et al. |
| 2008/0186138 A1 | 8/2008 | Butler et al. |
| 2008/0186139 A1 | 8/2008 | Butler et al. |
| 2008/0186166 A1 | 8/2008 | Zhou et al. |
| 2008/0186180 A1 | 8/2008 | Butler et al. |
| 2008/0188731 A1 | 8/2008 | Brister et al. |
| 2008/0188771 A1 | 8/2008 | Boecker et al. |
| 2008/0189051 A1 | 8/2008 | Goode et al. |
| 2008/0194925 A1 | 8/2008 | Alsafadi et al. |
| 2008/0194926 A1 | 8/2008 | Goh et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195641 A1 | 8/2008 | Tischer et al. |
| 2008/0195967 A1 | 8/2008 | Goode et al. |
| 2008/0197024 A1 | 8/2008 | Simpson et al. |
| 2008/0198020 A1 | 8/2008 | Fogg |
| 2008/0199011 A1 | 8/2008 | Tuyls et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208292 A1 | 8/2008 | Persen et al. |
| 2008/0211630 A1 | 9/2008 | Butler et al. |
| 2008/0211665 A1 | 9/2008 | Mazar et al. |
| 2008/0214915 A1 | 9/2008 | Brister et al. |
| 2008/0214918 A1 | 9/2008 | Brister et al. |
| 2008/0214946 A1 | 9/2008 | Miller et al. |
| 2008/0214949 A1 | 9/2008 | Stivoric et al. |
| 2008/0215121 A1 | 9/2008 | Bange et al. |
| 2008/0221555 A1 | 9/2008 | Sheppard et al. |
| 2008/0228051 A1 | 9/2008 | Shults et al. |
| 2008/0228054 A1 | 9/2008 | Shults et al. |
| 2008/0235469 A1 | 9/2008 | Drew |
| 2008/0242961 A1 | 10/2008 | Brister et al. |
| 2008/0249384 A1 | 10/2008 | Skyggebjerg et al. |
| 2008/0249470 A1 | 10/2008 | Malave et al. |
| 2008/0249590 A1 | 10/2008 | Simms |
| 2008/0252459 A1 | 10/2008 | Butler et al. |
| 2008/0255438 A1 | 10/2008 | Saidara et al. |
| 2008/0262333 A1 | 10/2008 | Staib et al. |
| 2008/0262469 A1 | 10/2008 | Brister et al. |
| 2008/0262573 A1 | 10/2008 | Seeberger et al. |
| 2008/0262989 A1 | 10/2008 | Su et al. |
| 2008/0264170 A1 | 10/2008 | Abbott |
| 2008/0269622 A1 | 10/2008 | Hatlestad |
| 2008/0272890 A1 | 11/2008 | Nitzan et al. |
| 2008/0275309 A1 | 11/2008 | Stivoric et al. |
| 2008/0275312 A1 | 11/2008 | Mosesov et al. |
| 2008/0275313 A1 | 11/2008 | Brister et al. |
| 2008/0278293 A1 | 11/2008 | Drucker |
| 2008/0278336 A1 | 11/2008 | Ortega et al. |
| 2008/0281298 A1 | 11/2008 | Andersen et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0287779 A1 | 11/2008 | Seiler et al. |
| 2008/0288026 A1 | 11/2008 | Cross et al. |
| 2008/0288029 A1 | 11/2008 | Healy et al. |
| 2008/0293455 A1 | 11/2008 | Forster et al. |
| 2008/0294028 A1 | 11/2008 | Brown |
| 2008/0296155 A1 | 12/2008 | Shults et al. |
| 2008/0297315 A1 | 12/2008 | Caruana |
| 2008/0306359 A1 | 12/2008 | Zdeblick et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0313896 A1 | 12/2008 | Shah et al. |
| 2008/0314395 A1 | 12/2008 | Kovatchev et al. |
| 2008/0318261 A2 | 12/2008 | Heller et al. |
| 2009/0005260 A1 | 1/2009 | Su et al. |
| 2009/0005666 A1 | 1/2009 | Shin et al. |
| 2009/0009293 A1 | 1/2009 | Drucker |
| 2009/0012374 A1 | 1/2009 | Schmelzeisen-Redeker et al. |
| 2009/0012379 A1 | 1/2009 | Goode et al. |
| 2009/0012473 A1 | 1/2009 | Stettler et al. |
| 2009/0012574 A1 | 1/2009 | Balczewski et al. |
| 2009/0018424 A1 | 1/2009 | Kamath et al. |
| 2009/0018425 A1 | 1/2009 | Ouyang et al. |
| 2009/0024009 A1 | 1/2009 | Freeman et al. |
| 2009/0027166 A1 | 1/2009 | Stevens et al. |
| 2009/0027297 A1 | 1/2009 | Zissel |
| 2009/0028074 A1 | 1/2009 | Knox |
| 2009/0030291 A1 | 1/2009 | O'Brien et al. |
| 2009/0030293 A1 | 1/2009 | Cooper et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0041626 A1 | 2/2009 | Atkin |
| 2009/0043181 A1 | 2/2009 | Brauker et al. |
| 2009/0043182 A1 | 2/2009 | Brauker et al. |
| 2009/0043525 A1 | 2/2009 | Brauker et al. |

| | | | | | |
|---|---|---|---|---|---|
| 2009/0043541 A1 | 2/2009 | Brauker et al. | 2009/0216460 A1 | 8/2009 | Abensour et al. |
| 2009/0043542 A1 | 2/2009 | Brauker et al. | 2009/0225310 A1 | 9/2009 | Yang et al. |
| 2009/0045055 A1 | 2/2009 | Rhodes et al. | 2009/0227855 A1 | 9/2009 | Hill et al. |
| 2009/0045916 A1 | 2/2009 | Nitzan et al. | 2009/0231125 A1 | 9/2009 | Baldus et al. |
| 2009/0048501 A1 | 2/2009 | Goodnow | 2009/0234213 A1 | 9/2009 | Hayes et al. |
| 2009/0048574 A1 | 2/2009 | Istoc et al. | 2009/0237215 A1 | 9/2009 | Dunlap et al. |
| 2009/0048646 A1 | 2/2009 | Katoozi et al. | 2009/0240120 A1 | 9/2009 | Mensinger et al. |
| 2009/0048870 A1 | 2/2009 | Godshall et al. | 2009/0240128 A1 | 9/2009 | Mensinger et al. |
| 2009/0054908 A1 | 2/2009 | Zand et al. | 2009/0240193 A1 | 9/2009 | Mensinger et al. |
| 2009/0062633 A1 | 3/2009 | Brauker et al. | 2009/0242399 A1 | 10/2009 | Kamath et al. |
| 2009/0062635 A1 | 3/2009 | Brauker et al. | 2009/0242425 A1 | 10/2009 | Kamath et al. |
| 2009/0067421 A1 | 3/2009 | Linden | 2009/0247838 A1 | 10/2009 | Cummings et al. |
| 2009/0071829 A1 | 3/2009 | O'Banion et al. | 2009/0247855 A1 | 10/2009 | Boock et al. |
| 2009/0076356 A1 | 3/2009 | Simpson et al. | 2009/0247856 A1 | 10/2009 | Boock et al. |
| 2009/0076358 A1 | 3/2009 | Reggiardo et al. | 2009/0247931 A1 | 10/2009 | Damgaard-Sorensen |
| 2009/0076360 A1 | 3/2009 | Brister et al. | 2009/0248112 A1 | 10/2009 | Mumbru et al. |
| 2009/0076361 A1 | 3/2009 | Kamath et al. | 2009/0252649 A1 | 10/2009 | Nomura |
| 2009/0083003 A1 | 3/2009 | Reggiardo | 2009/0264718 A1 | 10/2009 | Lesho |
| 2009/0085768 A1 | 4/2009 | Patel et al. | 2009/0264856 A1 | 10/2009 | Lebel et al. |
| 2009/0088077 A1 | 4/2009 | Brown et al. | 2009/0264964 A1 | 10/2009 | Abrahamson |
| 2009/0093985 A1 | 4/2009 | Burdett et al. | 2009/0270765 A1 | 10/2009 | Ghesquiere et al. |
| 2009/0099436 A1 | 4/2009 | Brister et al. | 2009/0270811 A1 | 10/2009 | Mounce et al. |
| 2009/0099506 A1 | 4/2009 | Estes et al. | 2009/0281598 A1 | 11/2009 | Haubrich et al. |
| 2009/0099509 A1 | 4/2009 | Estes et al. | 2009/0287073 A1 | 11/2009 | Boock et al. |
| 2009/0099864 A1 | 4/2009 | Cronrath et al. | 2009/0287074 A1 | 11/2009 | Shults et al. |
| 2009/0102611 A1 | 4/2009 | Quinn et al. | 2009/0292328 A1 | 11/2009 | Birkill et al. |
| 2009/0105554 A1 | 4/2009 | Stahmann et al. | 2009/0298704 A1 | 12/2009 | Anwar et al. |
| 2009/0105605 A1 | 4/2009 | Abreu | 2009/0299155 A1 | 12/2009 | Yang et al. |
| 2009/0105658 A1 | 4/2009 | Jennewine | 2009/0299156 A1 | 12/2009 | Simpson et al. |
| 2009/0112076 A1 | 4/2009 | Estes et al. | 2009/0299162 A1 | 12/2009 | Brauker et al. |
| 2009/0112478 A1 | 4/2009 | Mueller, Jr. et al. | 2009/0299276 A1 | 12/2009 | Brauker et al. |
| 2009/0112523 A1 | 4/2009 | Townsend et al. | 2009/0308531 A1 | 12/2009 | Raridan et al. |
| 2009/0118590 A1 | 5/2009 | Teller et al. | 2009/0309614 A1 | 12/2009 | Goodman et al. |
| 2009/0118592 A1 | 5/2009 | Klitgaard | 2009/0326610 A1 | 12/2009 | Pless et al. |
| 2009/0118596 A1 | 5/2009 | Khanuja et al. | 2010/0010324 A1 | 1/2010 | Brauker et al. |
| 2009/0118664 A1 | 5/2009 | Estes et al. | 2010/0010331 A1 | 1/2010 | Brauker et al. |
| 2009/0118665 A1 | 5/2009 | Estes et al. | 2010/0010332 A1 | 1/2010 | Brauker et al. |
| 2009/0121835 A1 | 5/2009 | Borret et al. | 2010/0012511 A1 | 1/2010 | Heller et al. |
| 2009/0122842 A1 | 5/2009 | Vavik | 2010/0012512 A1 | 1/2010 | Heller et al. |
| 2009/0124877 A1 | 5/2009 | Goode, Jr. et al. | 2010/0012514 A1 | 1/2010 | Heller et al. |
| 2009/0124878 A1 | 5/2009 | Goode et al. | 2010/0016687 A1 | 1/2010 | Brauker et al. |
| 2009/0124879 A1 | 5/2009 | Brister et al. | 2010/0016698 A1 | 1/2010 | Rasdal et al. |
| 2009/0124917 A1 | 5/2009 | Hatlestad et al. | 2010/0018867 A1 | 1/2010 | Heller et al. |
| 2009/0124964 A1 | 5/2009 | Leach et al. | 2010/0022855 A1 | 1/2010 | Brauker et al. |
| 2009/0131768 A1 | 5/2009 | Simpson et al. | 2010/0023092 A1 | 1/2010 | Govari et al. |
| 2009/0131769 A1 | 5/2009 | Leach et al. | 2010/0023093 A1 | 1/2010 | Govari et al. |
| 2009/0131776 A1 | 5/2009 | Simpson et al. | 2010/0026454 A1 | 2/2010 | Rowse et al. |
| 2009/0131777 A1 | 5/2009 | Simpson et al. | 2010/0030038 A1 | 2/2010 | Brauker et al. |
| 2009/0131860 A1 | 5/2009 | Nielsen et al. | 2010/0030053 A1 | 2/2010 | Goode, Jr. et al. |
| 2009/0137886 A1 | 5/2009 | Shariati et al. | 2010/0030484 A1 | 2/2010 | Brauker et al. |
| 2009/0137887 A1 | 5/2009 | Shariati et al. | 2010/0030485 A1 | 2/2010 | Brauker et al. |
| 2009/0143659 A1 | 6/2009 | Li et al. | 2010/0036215 A1 | 2/2010 | Goode, Jr. et al. |
| 2009/0143660 A1 | 6/2009 | Brister et al. | 2010/0036216 A1 | 2/2010 | Goode, Jr. et al. |
| 2009/0143662 A1 | 6/2009 | Estes et al. | 2010/0036222 A1 | 2/2010 | Goode, Jr. et al. |
| 2009/0149723 A1 | 6/2009 | Krauss et al. | 2010/0036223 A1 | 2/2010 | Goode, Jr. et al. |
| 2009/0149803 A1 | 6/2009 | Estes et al. | 2010/0036225 A1 | 2/2010 | Goode, Jr. et al. |
| 2009/0150186 A1 | 6/2009 | Cohen et al. | 2010/0041971 A1 | 2/2010 | Goode, Jr. et al. |
| 2009/0156919 A1 | 6/2009 | Brister et al. | 2010/0045465 A1 | 2/2010 | Brauker et al. |
| 2009/0156924 A1 | 6/2009 | Shariati et al. | 2010/0049010 A1 | 2/2010 | Goldreich |
| 2009/0163790 A1 | 6/2009 | Brister et al. | 2010/0049024 A1 | 2/2010 | Saint et al. |
| 2009/0163791 A1 | 6/2009 | Brister et al. | 2010/0063373 A1 | 3/2010 | Kamath et al. |
| 2009/0177068 A1 | 7/2009 | Stivoric et al. | 2010/0063374 A1 | 3/2010 | Goodnow et al. |
| 2009/0177103 A1 | 7/2009 | Bharmi | 2010/0076283 A1 | 3/2010 | Simpson et al. |
| 2009/0178459 A1 | 7/2009 | Li et al. | 2010/0076288 A1 | 3/2010 | Connolly et al. |
| 2009/0180513 A1 | 7/2009 | Schick et al. | 2010/0076412 A1 | 3/2010 | Rush et al. |
| 2009/0181625 A1 | 7/2009 | Twitchell, Jr. | 2010/0081908 A1 | 4/2010 | Dobbles et al. |
| 2009/0182206 A1 | 7/2009 | Najafi et al. | 2010/0081910 A1 | 4/2010 | Brister et al. |
| 2009/0182217 A1 | 7/2009 | Li et al. | 2010/0087724 A1 | 4/2010 | Brauker et al. |
| 2009/0192366 A1 | 7/2009 | Mensinger et al. | 2010/0096259 A1 | 4/2010 | Zhang et al. |
| 2009/0192380 A1 | 7/2009 | Shariati et al. | 2010/0099970 A1 | 4/2010 | Shults et al. |
| 2009/0192574 A1 | 7/2009 | Von Arx et al. | 2010/0099971 A1 | 4/2010 | Shults et al. |
| 2009/0192722 A1 | 7/2009 | Shariati et al. | 2010/0099972 A1 | 4/2010 | Goodnow |
| 2009/0192724 A1 | 7/2009 | Brauker et al. | 2010/0099973 A1 | 4/2010 | Goodnow |
| 2009/0192745 A1 | 7/2009 | Kamath et al. | 2010/0100050 A1 | 4/2010 | Cane |
| 2009/0192751 A1 | 7/2009 | Kamath et al. | 2010/0114233 A1 | 5/2010 | Von Arx et al. |
| 2009/0203981 A1 | 8/2009 | Brauker et al. | 2010/0119693 A1 | 5/2010 | Tapsak et al. |
| 2009/0204341 A1 | 8/2009 | Brauker et al. | 2010/0121169 A1 | 5/2010 | Petisce et al. |
| 2009/0209904 A1 | 8/2009 | Peeters | 2010/0137699 A1 | 6/2010 | Sher |
| 2009/0216103 A1 | 8/2009 | Brister et al. | 2010/0161269 A1 | 6/2010 | Kamath et al. |

| | | | | | | | |
|---|---|---|---|---|---|---|---|
| 2010/0168540 | A1 | 7/2010 | Kamath et al. | EP | 1050321 | 11/2000 | |
| 2010/0168541 | A1 | 7/2010 | Kamath et al. | EP | 0707825 | 12/2000 | |
| 2010/0168542 | A1 | 7/2010 | Kamath et al. | EP | 1060704 | 12/2000 | |
| 2010/0168543 | A1 | 7/2010 | Kamath et al. | EP | 1083519 | 3/2001 | |
| 2010/0168544 | A1 | 7/2010 | Kamath et al. | EP | 0710906 | 5/2001 | |
| 2010/0168545 | A1 | 7/2010 | Kamath et al. | EP | 0812752 | 9/2001 | |
| 2010/0168657 | A1 | 7/2010 | Kamath et al. | EP | 1154267 | 11/2001 | |
| 2010/0174158 | A1 | 7/2010 | Kamath et al. | EP | 0836165 | 12/2001 | |
| 2010/0174166 | A1 | 7/2010 | Brister et al. | EP | 0950288 | 1/2002 | |
| 2010/0174167 | A1 | 7/2010 | Kamath et al. | EP | 1174163 | 1/2002 | |
| 2010/0174168 | A1 | 7/2010 | Goode, Jr. et al. | EP | 0707867 | 6/2002 | |
| 2010/0179399 | A1 | 7/2010 | Goode, Jr. et al. | EP | 1216653 | 6/2002 | |
| 2010/0179402 | A1 | 7/2010 | Goode, Jr. et al. | EP | 0817809 | 7/2002 | |
| 2010/0179404 | A1 | 7/2010 | Kamath et al. | EP | 0724236 | 10/2002 | |
| 2010/0179405 | A1 | 7/2010 | Goode, Jr. et al. | EP | 1252860 | 10/2002 | |
| 2010/0179408 | A1 | 7/2010 | Kamath et al. | EP | 0958495 | 11/2002 | |
| 2010/0179409 | A1 | 7/2010 | Kamath et al. | EP | 0968415 | 11/2002 | |
| 2010/0185065 | A1 | 7/2010 | Goode, Jr. et al. | EP | 1260815 | 11/2002 | |
| 2010/0185073 | A1 | 7/2010 | Goode, Jr. et al. | EP | 0777506 | 12/2002 | |
| 2010/0185074 | A1 | 7/2010 | Goode, Jr. et al. | EP | 1288653 | 3/2003 | |
| 2010/0185075 | A1 | 7/2010 | Brister | EP | 0685825 | 4/2003 | |
| 2010/0198035 | A1 | 8/2010 | Kamath et al. | EP | 1308872 | 5/2003 | |
| 2010/0198036 | A1 | 8/2010 | Kamath et al. | EP | 1102559 | 6/2003 | |
| 2010/0217106 | A1 | 8/2010 | Goode, Jr. et al. | EP | 0780822 | 7/2003 | |
| 2010/0217557 | A1 | 8/2010 | Kamath et al. | EP | 1077634 | 7/2003 | |
| 2010/0223013 | A1 | 9/2010 | Kamath et al. | EP | 1078258 | 7/2003 | |
| 2010/0223022 | A1 | 9/2010 | Kamath et al. | EP | 1078329 | 7/2003 | |
| 2010/0223023 | A1 | 9/2010 | Kamath et al. | EP | 0699046 | 8/2003 | |
| 2010/0228109 | A1 | 9/2010 | Kamath et al. | EP | 1338295 | 8/2003 | |
| | | | | EP | 0841448 | 12/2003 | |
| FOREIGN PATENT DOCUMENTS | | | | EP | 0863489 | 12/2003 | |
| CA | | 2396749 | 7/2001 | EP | 1188144 | 12/2003 | |
| CA | | 2454655 | 2/2003 | EP | 1372102 | 12/2003 | |
| CA | | 2496579 | 3/2004 | EP | 1077636 | 1/2004 | |
| CA | | 2143172 | 7/2005 | EP | 1222742 | 4/2004 | |
| CA | | 2550855 | 7/2005 | EP | 1408863 | 4/2004 | |
| CA | | 2572787 | 1/2006 | EP | 1411644 | 4/2004 | |
| EP | | 0183351 | 6/1986 | EP | 1413245 | 4/2004 | |
| EP | | 0289136 | 11/1988 | EP | 1421896 | 5/2004 | |
| EP | | 0396788 | 11/1990 | EP | 1144028 | 6/2004 | |
| EP | | 0453283 | 10/1991 | EP | 1424098 | 6/2004 | |
| EP | | 0511807 | 11/1992 | EP | 1430831 | 6/2004 | |
| EP | | 0258415 | 12/1992 | EP | 1431758 | 6/2004 | |
| EP | | 0554955 | 8/1993 | EP | 1178841 | 7/2004 | |
| EP | | 0563713 | 10/1993 | EP | 1171201 | 8/2004 | |
| EP | | 0274526 | 12/1993 | EP | 1259288 | 8/2004 | |
| EP | | 0619101 | 10/1994 | EP | 1128871 | 10/2004 | |
| EP | | 0393103 | 6/1995 | EP | 1136033 | 11/2004 | |
| EP | | 0393089 | 7/1995 | EP | 1211630 | 12/2004 | |
| EP | | 0707824 | 4/1996 | EP | 0781473 | 1/2005 | |
| EP | | 0710465 | 5/1996 | EP | 1019715 | 1/2005 | |
| EP | | 0458821 | 7/1996 | EP | 1498067 | 1/2005 | |
| EP | | 0724859 | 8/1996 | EP | 1502543 | 2/2005 | |
| EP | | 0745747 | 12/1996 | EP | 1508296 | 2/2005 | |
| EP | | 0535898 | 2/1997 | EP | 1508299 | 2/2005 | |
| EP | | 0526173 | 5/1997 | EP | 0953181 | 3/2005 | |
| EP | | 0570674 | 5/1997 | EP | 1130996 | 4/2005 | |
| EP | | 0771575 | 5/1997 | EP | 1526543 | 4/2005 | |
| EP | | 0771867 | 5/1997 | EP | 0749332 | 5/2005 | |
| EP | | 0537378 | 9/1997 | EP | 1295367 | 5/2005 | |
| EP | | 0706407 | 9/1997 | EP | 1436044 | 5/2005 | |
| EP | | 0813320 | 12/1997 | EP | 1530115 | 5/2005 | |
| EP | | 0851639 | 7/1998 | EP | 1530316 | 5/2005 | |
| EP | | 0398695 | 9/1998 | EP | 1555527 | 7/2005 | |
| EP | | 0429617 | 9/1998 | EP | 1115435 | 8/2005 | |
| EP | | 0557297 | 2/1999 | EP | 1564839 | 8/2005 | |
| EP | | 0787984 | 4/1999 | EP | 1569352 | 8/2005 | |
| EP | | 0834146 | 5/1999 | EP | 1154717 | 9/2005 | |
| EP | | 0915573 | 5/1999 | EP | 1587017 | 10/2005 | |
| EP | | 0677210 | 10/1999 | EP | 1292217 | 11/2005 | |
| EP | | 0640939 | 4/2000 | EP | 1011792 | 12/2005 | |
| EP | | 0678308 | 5/2000 | EP | 1216654 | 12/2005 | |
| EP | | 1011425 | 6/2000 | EP | 1350462 | 12/2005 | |
| EP | | 1011804 | 6/2000 | EP | 1609501 | 12/2005 | |
| EP | | 1012956 | 6/2000 | EP | 1339312 | 1/2006 | |
| EP | | 1037515 | 9/2000 | EP | 1611834 | 1/2006 | |
| EP | | 0613390 | 10/2000 | EP | 1611835 | 1/2006 | |
| EP | | 0766578 | 10/2000 | EP | 1611838 | 1/2006 | |
| EP | | 1048264 | 11/2000 | EP | 1611839 | 1/2006 | |

| | | | | | |
|---|---|---|---|---|---|
| EP | 1666091 | 6/2006 | WO | WO-00/16689 | 3/2000 |
| EP | 1703697 | 9/2006 | WO | WO-00/18449 | 4/2000 |
| EP | 1704893 | 9/2006 | WO | WO-00/19887 | 4/2000 |
| EP | 1437937 | 5/2008 | WO | WO-00/21434 | 4/2000 |
| EP | 1489961 | 9/2010 | WO | WO-00/23941 | 4/2000 |
| EP | 1513585 | 1/2011 | WO | WO-00/23943 | 4/2000 |
| GB | 2335743 | 9/1999 | WO | WO-00/25662 | 5/2000 |
| WO | WO-86/05675 | 10/1986 | WO | WO-00/26856 | 5/2000 |
| WO | WO-87/04900 | 8/1987 | WO | WO-00/26993 | 5/2000 |
| WO | WO-87/06342 | 10/1987 | WO | WO-00/30529 | 6/2000 |
| WO | WO-88/00785 | 1/1988 | WO | WO-00/30532 | 6/2000 |
| WO | WO-90/00738 | 1/1990 | WO | WO-00/30534 | 6/2000 |
| WO | WO-90/03070 | 3/1990 | WO | WO-00/32095 | 6/2000 |
| WO | WO-90/09707 | 8/1990 | WO | WO-00/32105 | 6/2000 |
| WO | WO-90/14736 | 11/1990 | WO | WO-00/32258 | 6/2000 |
| WO | WO-91/16416 | 10/1991 | WO | WO-00/36974 | 6/2000 |
| WO | WO-92/03705 | 3/1992 | WO | WO-00/41319 | 7/2000 |
| WO | WO-92/13271 | 8/1992 | WO | WO-00/41404 | 7/2000 |
| WO | WO-92/17866 | 10/1992 | WO | WO-00/45696 | 8/2000 |
| WO | WO-93/05489 | 3/1993 | WO | WO-00/47109 | 8/2000 |
| WO | WO-94/04094 | 3/1994 | WO | WO-00/49940 | 8/2000 |
| WO | WO-94/05371 | 3/1994 | WO | WO-00/49941 | 8/2000 |
| WO | WO-94/12238 | 6/1994 | WO | WO-00/50849 | 8/2000 |
| WO | WO-94/16471 | 7/1994 | WO | WO-00/52444 | 9/2000 |
| WO | WO-94/20941 | 9/1994 | WO | WO-00/52498 | 9/2000 |
| WO | WO-94/24548 | 10/1994 | WO | WO-00/56210 | 9/2000 |
| WO | WO-94/24929 | 11/1994 | WO | WO-00/58730 | 10/2000 |
| WO | WO-95/16393 | 6/1995 | WO | WO-00/59370 | 10/2000 |
| WO | WO-95/24233 | 9/1995 | WO | WO-00/59376 | 10/2000 |
| WO | WO-96/11722 | 4/1996 | WO | WO-00/62663 | 10/2000 |
| WO | WO-96/12435 | 5/1996 | WO | WO-00/62664 | 10/2000 |
| WO | WO-96/13914 | 5/1996 | WO | WO-00/62665 | 10/2000 |
| WO | WO-96/19774 | 6/1996 | WO | WO-00/62861 | 10/2000 |
| WO | WO-96/39977 | 12/1996 | WO | WO-00/68670 | 11/2000 |
| WO | WO-96/41203 | 12/1996 | WO | WO-00/69663 | 11/2000 |
| WO | WO-96/41290 | 12/1996 | WO | WO-00/70552 | 11/2000 |
| WO | WO-97/18639 | 5/1997 | WO | WO-00/70569 | 11/2000 |
| WO | WO-97/19344 | 5/1997 | WO | WO-00/74753 | 12/2000 |
| WO | WO-97/33513 | 9/1997 | WO | WO-00/78210 | 12/2000 |
| WO | WO-97/37218 | 10/1997 | WO | WO-01/00085 | 1/2001 |
| WO | WO-97/43740 | 11/1997 | WO | WO-01/01366 | 1/2001 |
| WO | WO-98/02837 | 1/1998 | WO | WO-01/12092 | 2/2001 |
| WO | WO-98/05171 | 2/1998 | WO | WO-01/12108 | 2/2001 |
| WO | WO-98/16895 | 4/1998 | WO | WO-01/13999 | 3/2001 |
| WO | WO-98/26282 | 6/1998 | WO | WO-01/14010 | 3/2001 |
| WO | WO-98/26342 | 6/1998 | WO | WO-01/17453 | 3/2001 |
| WO | WO-98/27441 | 6/1998 | WO | WO-01/22874 | 4/2001 |
| WO | WO-98/27670 | 6/1998 | WO | WO-01/26068 | 4/2001 |
| WO | WO-98/28715 | 7/1998 | WO | WO-01/28105 | 4/2001 |
| WO | WO-98/32094 | 7/1998 | WO | WO-01/28416 | 4/2001 |
| WO | WO-98/37926 | 9/1998 | WO | WO-01/37726 | 5/2001 |
| WO | WO-98/38906 | 9/1998 | WO | WO-01/49368 | 7/2001 |
| WO | WO-98/39655 | 9/1998 | WO | WO-01/50433 | 7/2001 |
| WO | WO-98/39749 | 9/1998 | WO | WO-01/52180 | 7/2001 |
| WO | WO-98/41847 | 9/1998 | WO | WO-01/52351 | 7/2001 |
| WO | WO-98/43700 | 10/1998 | WO | WO-01/52727 | 7/2001 |
| WO | WO-98/43701 | 10/1998 | WO | WO-01/52934 | 7/2001 |
| WO | WO-98/58323 | 12/1998 | WO | WO-01/52935 | 7/2001 |
| WO | WO-98/59487 | 12/1998 | WO | WO-01/54753 | 8/2001 |
| WO | WO-99/05750 | 2/1999 | WO | WO-01/55952 | 8/2001 |
| WO | WO-99/08105 | 2/1999 | WO | WO-01/58252 | 8/2001 |
| WO | WO-99/10520 | 3/1999 | WO | WO-01/58389 | 8/2001 |
| WO | WO-99/13765 | 3/1999 | WO | WO-01/61883 | 8/2001 |
| WO | WO-99/29230 | 6/1999 | WO | WO-01/62142 | 8/2001 |
| WO | WO-99/30144 | 6/1999 | WO | WO-01/67625 | 9/2001 |
| WO | WO-99/33193 | 7/1999 | WO | WO-01/73956 | 10/2001 |
| WO | WO-99/39298 | 8/1999 | WO | WO-01/78831 | 10/2001 |
| WO | WO-99/47905 | 9/1999 | WO | WO-01/80731 | 11/2001 |
| WO | WO-99/48419 | 9/1999 | WO | WO-01/88518 | 11/2001 |
| WO | WO-99/53287 | 10/1999 | WO | WO-01/88534 | 11/2001 |
| WO | WO-99/56613 | 11/1999 | WO | WO-01/91080 | 11/2001 |
| WO | WO-99/58050 | 11/1999 | WO | WO-01/91626 | 12/2001 |
| WO | WO-99/58051 | 11/1999 | WO | WO-01/96986 | 12/2001 |
| WO | WO-99/58973 | 11/1999 | WO | WO-01/97686 | 12/2001 |
| WO | WO-99/66997 | 12/1999 | WO | WO-01/97907 | 12/2001 |
| WO | WO-00/04945 | 2/2000 | WO | WO-01/74447 | 1/2002 |
| WO | WO-00/10628 | 3/2000 | WO | WO-02/00111 | 1/2002 |
| WO | WO-00/13585 | 3/2000 | WO | WO-02/02005 | 1/2002 |
| WO | WO-00/15103 | 3/2000 | WO | WO-02/05391 | 1/2002 |

| | | | | | | |
|---|---|---|---|---|---|---|
| WO | WO-02/05702 | 1/2002 | | WO | WO-03/057027 | 7/2003 |
| WO | WO-02/07496 | 1/2002 | | WO | WO-03/059145 | 7/2003 |
| WO | WO-02/07596 | 1/2002 | | WO | WO-03/063956 | 8/2003 |
| WO | WO-02/07816 | 1/2002 | | WO | WO-03/063964 | 8/2003 |
| WO | WO-02/13686 | 2/2002 | | WO | WO-03/066163 | 8/2003 |
| WO | WO-02/15777 | 2/2002 | | WO | WO-03/069798 | 8/2003 |
| WO | WO-02/15778 | 2/2002 | | WO | WO-03/021548 | 9/2003 |
| WO | WO-02/17210 | 2/2002 | | WO | WO-03/071923 | 9/2003 |
| WO | WO-02/20073 | 3/2002 | | WO | WO-03/071930 | 9/2003 |
| WO | WO-02/24065 | 3/2002 | | WO | WO-03/074887 | 9/2003 |
| WO | WO-02/25825 | 3/2002 | | WO | WO-03/075744 | 9/2003 |
| WO | WO-02/26115 | 4/2002 | | WO | WO-03/076893 | 9/2003 |
| WO | WO-02/28022 | 4/2002 | | WO | WO-03/077364 | 9/2003 |
| WO | WO-02/28454 | 4/2002 | | WO | WO-03/077745 | 9/2003 |
| WO | WO-02/29929 | 4/2002 | | WO | WO-03/077752 | 9/2003 |
| WO | WO-02/34331 | 5/2002 | | WO | WO-03/080157 | 10/2003 |
| WO | WO-02/35997 | 5/2002 | | WO | WO-03/081934 | 10/2003 |
| WO | WO-02/41231 | 5/2002 | | WO | WO-03/082098 | 10/2003 |
| WO | WO-02/41237 | 5/2002 | | WO | WO-03/085617 | 10/2003 |
| WO | WO-02/45842 | 6/2002 | | WO | WO-03/086184 | 10/2003 |
| WO | WO-02/47465 | 6/2002 | | WO | WO-03/088830 | 10/2003 |
| WO | WO-02/054013 | 7/2002 | | WO | WO-03/088835 | 10/2003 |
| WO | WO-02/054945 | 7/2002 | | WO | WO-03/035891 | 11/2003 |
| WO | WO-02/056151 | 7/2002 | | WO | WO-03/036255 | 11/2003 |
| WO | WO-02/056763 | 7/2002 | | WO | WO-03/091746 | 11/2003 |
| WO | WO-02/058551 | 8/2002 | | WO | WO-03/091943 | 11/2003 |
| WO | WO-02/060371 | 8/2002 | | WO | WO-03/092119 | 11/2003 |
| WO | WO-02/062215 | 8/2002 | | WO | WO-03/092172 | 11/2003 |
| WO | WO-02/064032 | 8/2002 | | WO | WO-03/094714 | 11/2003 |
| WO | WO-02/067122 | 8/2002 | | WO | WO-03/095023 | 11/2003 |
| WO | WO-02/068047 | 9/2002 | | WO | WO-03/095024 | 11/2003 |
| WO | WO-02/069236 | 9/2002 | | WO | WO-2004/007756 | 1/2004 |
| WO | WO-02/053764 | 10/2002 | | WO | WO-2004/008094 | 1/2004 |
| WO | WO-02/078537 | 10/2002 | | WO | WO-2004/008956 | 1/2004 |
| WO | WO-02/080483 | 10/2002 | | WO | WO-2004/009161 | 1/2004 |
| WO | WO-02/082984 | 10/2002 | | WO | WO-2004/019172 | 3/2004 |
| WO | WO-02/086837 | 10/2002 | | WO | WO-2004/023415 | 3/2004 |
| WO | WO-02/087681 | 11/2002 | | WO | WO-2004/023974 | 3/2004 |
| WO | WO-02/093881 | 11/2002 | | WO | WO-2004/027363 | 4/2004 |
| WO | WO-02/097419 | 12/2002 | | WO | WO-2004/030727 | 4/2004 |
| WO | WO-02/099822 | 12/2002 | | WO | WO-2004/032715 | 4/2004 |
| WO | WO-02/100457 | 12/2002 | | WO | WO-2004/034221 | 4/2004 |
| WO | WO-03/000127 | 1/2003 | | WO | WO-2004/039102 | 5/2004 |
| WO | WO-03/004249 | 1/2003 | | WO | WO-2004/039450 | 5/2004 |
| WO | WO-03/004975 | 1/2003 | | WO | WO-2004/014484 | 6/2004 |
| WO | WO-03/005891 | 1/2003 | | WO | WO-2004/047630 | 6/2004 |
| WO | WO-03/006091 | 1/2003 | | WO | WO-2004/047914 | 6/2004 |
| WO | WO-03/008013 | 1/2003 | | WO | WO-2004/053491 | 6/2004 |
| WO | WO-03/008014 | 1/2003 | | WO | WO-2004/054430 | 7/2004 |
| WO | WO-03/009207 | 1/2003 | | WO | WO-2004/056266 | 7/2004 |
| WO | WO-03/009208 | 1/2003 | | WO | WO-2004/058060 | 7/2004 |
| WO | WO-03/011131 | 2/2003 | | WO | WO-2004/059551 | 7/2004 |
| WO | WO-03/013076 | 2/2003 | | WO | WO-2004/059589 | 7/2004 |
| WO | WO-03/015005 | 2/2003 | | WO | WO-2004/060043 | 7/2004 |
| WO | WO-03/015838 | 2/2003 | | WO | WO-2004/060144 | 7/2004 |
| WO | WO-03/016711 | 2/2003 | | WO | WO-2004/060297 | 7/2004 |
| WO | WO-03/019450 | 3/2003 | | WO | WO-2004/060455 | 7/2004 |
| WO | WO-03/022327 | 3/2003 | | WO | WO-2004/061753 | 7/2004 |
| WO | WO-03/023386 | 3/2003 | | WO | WO-2004/062131 | 7/2004 |
| WO | WO-03/023979 | 3/2003 | | WO | WO-2004/066834 | 8/2004 |
| WO | WO-03/024322 | 3/2003 | | WO | WO-2004/069095 | 8/2004 |
| WO | WO-03/008037 | 5/2003 | | WO | WO-2004/069164 | 8/2004 |
| WO | WO-03/036552 | 5/2003 | | WO | WO-2004/070546 | 8/2004 |
| WO | WO-03/038747 | 5/2003 | | WO | WO-2004/070548 | 8/2004 |
| WO | WO-03/040950 | 5/2003 | | WO | WO-2004/070549 | 8/2004 |
| WO | WO-03/043494 | 5/2003 | | WO | WO-2004/070556 | 8/2004 |
| WO | WO-03/043684 | 5/2003 | | WO | WO-2004/070557 | 8/2004 |
| WO | WO-03/043688 | 5/2003 | | WO | WO-2004/070562 | 8/2004 |
| WO | WO-03/045224 | 6/2003 | | WO | WO-2004/070876 | 8/2004 |
| WO | WO-03/047426 | 6/2003 | | WO | WO-2004/070994 | 8/2004 |
| WO | WO-03/048998 | 6/2003 | | WO | WO-2004/070995 | 8/2004 |
| WO | WO-03/049597 | 6/2003 | | WO | WO-2004/072892 | 8/2004 |
| WO | WO-03/050643 | 6/2003 | | WO | WO-2004/073491 | 9/2004 |
| WO | WO-03/049592 | 7/2003 | | WO | WO-2004/074788 | 9/2004 |
| WO | WO-03/053498 | 7/2003 | | WO | WO-2004/075101 | 9/2004 |
| WO | WO-03/053515 | 7/2003 | | WO | WO-2004/077052 | 9/2004 |
| WO | WO-03/054825 | 7/2003 | | WO | WO-2004/079644 | 9/2004 |
| WO | WO-03/056033 | 7/2003 | | WO | WO-2004/049280 | 10/2004 |
| WO | WO-03/056354 | 7/2003 | | WO | WO-2004/090661 | 10/2004 |

| | | |
|---|---|---|
| WO | WO-2004/091419 | 10/2004 |
| WO | WO-2004/098390 | 11/2004 |
| WO | WO-2004/110256 | 12/2004 |
| WO | WO-2005/000391 | 1/2005 |
| WO | WO-2005/000397 | 1/2005 |
| WO | WO-2005/002108 | 1/2005 |
| WO | WO-2005/007879 | 1/2005 |
| WO | WO-2005/009514 | 2/2005 |
| WO | WO-2005/010483 | 2/2005 |
| WO | WO-2005/010796 | 2/2005 |
| WO | WO-2005/010925 | 2/2005 |
| WO | WO-2005/011489 | 2/2005 |
| WO | WO-2005/011490 | 2/2005 |
| WO | WO-2005/011520 | 2/2005 |
| WO | WO-2005/012871 | 2/2005 |
| WO | WO-2005/012873 | 2/2005 |
| WO | WO-2004/036183 | 3/2005 |
| WO | WO-2005/018443 | 3/2005 |
| WO | WO-2005/018450 | 3/2005 |
| WO | WO-2005/029242 | 3/2005 |
| WO | WO-2005/033701 | 4/2005 |
| WO | WO-2005/036448 | 4/2005 |
| WO | WO-2005/037365 | 4/2005 |
| WO | WO-2005/037370 | 4/2005 |
| WO | WO-2005/040793 | 5/2005 |
| WO | WO-2005/041131 | 5/2005 |
| WO | WO-2005/041766 | 5/2005 |
| WO | WO-2005/042092 | 5/2005 |
| WO | WO-2005/042095 | 5/2005 |
| WO | WO-2005/042096 | 5/2005 |
| WO | WO-2005/042097 | 5/2005 |
| WO | WO-2005/042098 | 5/2005 |
| WO | WO-2005/045394 | 5/2005 |
| WO | WO-2005/045744 | 5/2005 |
| WO | WO-2005/046467 | 5/2005 |
| WO | WO-2005/047837 | 5/2005 |
| WO | WO-2005/036175 | 6/2005 |
| WO | WO-2005/048809 | 6/2005 |
| WO | WO-2005/048830 | 6/2005 |
| WO | WO-2005/053525 | 6/2005 |
| WO | WO-2005/057168 | 6/2005 |
| WO | WO-2005/057173 | 6/2005 |
| WO | WO-2005/057481 | 6/2005 |
| WO | WO-2005/060219 | 6/2005 |
| WO | WO-2005/060221 | 6/2005 |
| WO | WO-2005/060222 | 6/2005 |
| WO | WO-2005/060335 | 7/2005 |
| WO | WO-2005/061048 | 7/2005 |
| WO | WO-2005/063118 | 7/2005 |
| WO | WO-2005/065363 | 7/2005 |
| WO | WO-2005/065537 | 7/2005 |
| WO | WO-2005/067161 | 7/2005 |
| WO | WO-2005/048834 | 8/2005 |
| WO | WO-2005/065738 | 8/2005 |
| WO | WO-2005/070289 | 8/2005 |
| WO | WO-2005/074161 | 8/2005 |
| WO | WO-2005/074821 | 8/2005 |
| WO | WO-2005/057175 | 9/2005 |
| WO | WO-2005/079664 | 9/2005 |
| WO | WO-2005/082235 | 9/2005 |
| WO | WO-2005/082436 | 9/2005 |
| WO | WO-2005/083621 | 9/2005 |
| WO | WO-2005/089103 | 9/2005 |
| WO | WO-2005/091205 | 9/2005 |
| WO | WO-2005/032338 | 10/2005 |
| WO | WO-2005/092177 | 10/2005 |
| WO | WO-2005/093456 | 10/2005 |
| WO | WO-2005/093629 | 10/2005 |
| WO | WO-2005/093635 | 10/2005 |
| WO | WO-2005/099816 | 10/2005 |
| WO | WO-2005/099817 | 10/2005 |
| WO | WO-2005/101279 | 10/2005 |
| WO | WO-2005/065538 | 11/2005 |
| WO | WO-2005/091546 | 11/2005 |
| WO | WO-2005/104022 | 11/2005 |
| WO | WO-2005/106760 | 11/2005 |
| WO | WO-2005/107313 | 11/2005 |
| WO | WO-2005/110536 | 11/2005 |
| WO | WO-2005/111086 | 11/2005 |
| WO | WO-2005/112283 | 11/2005 |
| WO | WO-2005/065542 | 12/2005 |
| WO | WO-2005/112741 | 12/2005 |
| WO | WO-2005/112744 | 12/2005 |
| WO | WO-2005/115533 | 12/2005 |
| WO | WO-2005/115538 | 12/2005 |
| WO | WO-2005/118027 | 12/2005 |
| WO | WO-2005/119524 | 12/2005 |
| WO | WO-2005/119555 | 12/2005 |
| WO | WO-2005/120336 | 12/2005 |
| WO | WO-2005/121769 | 12/2005 |
| WO | WO-2005/121785 | 12/2005 |
| WO | WO-2006/001929 | 1/2006 |
| WO | WO-2006/003648 | 1/2006 |
| WO | WO-2006/006159 | 1/2006 |
| WO | WO-2006/010108 | 1/2006 |
| WO | WO-2006/012364 | 2/2006 |
| WO | WO-2006/026741 | 3/2006 |
| WO | WO-2006/032653 | 3/2006 |
| WO | WO-2006/069675 | 7/2006 |
| WO | WO-2006/086423 | 8/2006 |
| WO | WO-2006/124099 | 11/2006 |

OTHER PUBLICATIONS

PCT Application No. PCT/US2006/004355, International Search Report mailed May 2, 2007.
PCT Application No. PCT/US2006/004355, International Preliminary Report on Patentability and Written Opinion of the International Searching Authority mailed Aug. 14, 2007.
Internet Printout: http:rfid-handbook.com, printed Feb. 6, 2006.
Internet Printout: http:rfid-handbook.com, printed Feb. 7, 2006.
U.S. Appl. No. 12/476,921, Notice of Allowance mailed Oct. 27, 2011.
U.S. Appl. No. 12/625,522, Office Action mailed Nov. 14, 2011.
U.S. Appl. No. 11/350,398, Notice of Allowance mailed Apr. 8, 2009.
U.S. Appl. No. 11/350,398, Office Action mailed Sep. 19, 2008.
U.S. Appl. No. 12/476,921, Office Action mailed Mar. 31, 2011.
US 7,530,950, 05/2009, Brister et al. (withdrawn)

* cited by examiner

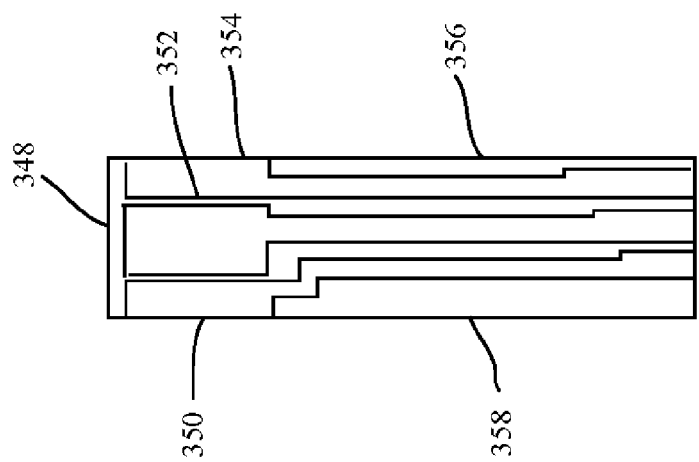
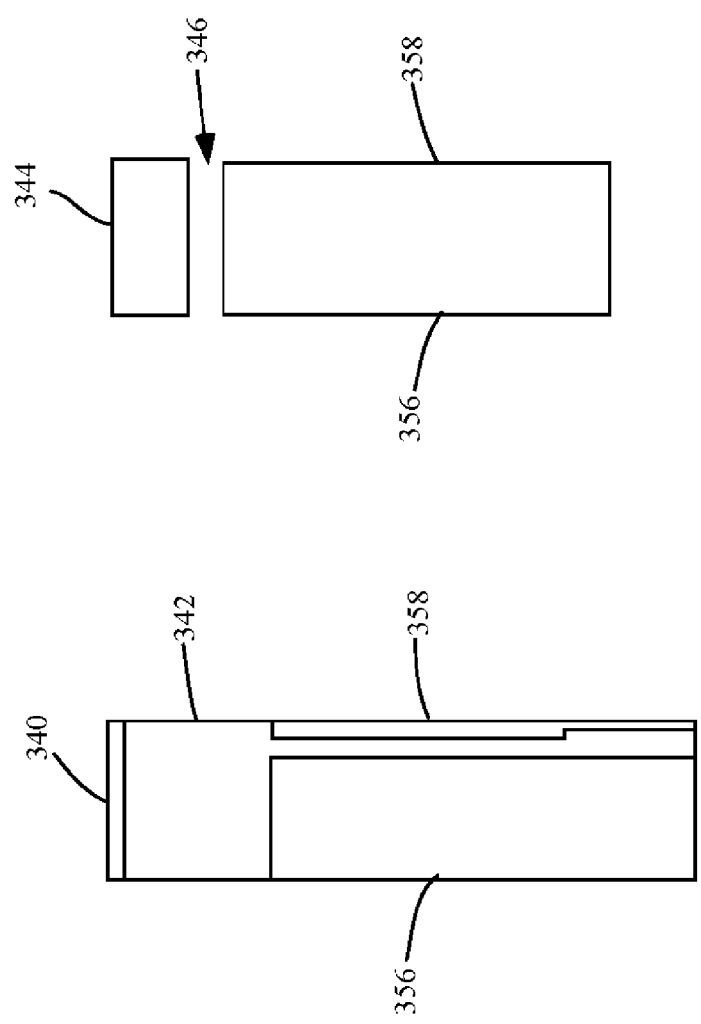
FIGURE 3A  FIGURE 3B  FIGURE 3C

RF TAG ON TEST STRIPS, TEST STRIP VIALS AND BOXES

RELATED APPLICATION

The present application is a continuation of U.S. patent application Ser. No. 12/476,921 filed Jun. 2, 2009, which is a continuation of U.S. patent application Ser. No. 11/350,398 filed Feb. 7, 2006, now U.S. Pat. No. 7,545,272, which claims priority to U.S. provisional application Nos. 60/701,654 filed Jul. 21, 2005 and 60/650,912 filed Feb. 8, 2005, the disclosures of each of which are incorporated herein by reference for all purposes.

BACKGROUND

Diabetes care involves periodically checking the blood glucose level of a bodily fluid such as blood. Based on the measured bodily fluid level, a diabetic may take one or more steps such as injecting insulin or consuming carbohydrates to bring the level back to a desired level.

Glucose Meters

FIG. 1 illustrates a conventional blood glucose meter 100 (see U.S. Design Pat. No. D393,313, which is hereby incorporated by reference). The meter 100 includes a test strip slot 102, a display 104 and one or more operational buttons 106. Although not shown in FIG. 1, the meter 100 also includes component circuitry for receiving signals that depend on the glucose level of a fluid applied to a strip that is inserted into the slot 102, and component circuitry for determining the glucose level based on the received signals. FIG. 2 illustrates a blood glucose meter 200 with display 104 and operational buttons 106, and also having a glucose test strip 202 inserted into a slot 102 for testing a body fluid sample applied to the strip 202.

Glucose Sensors

Small volume (e.g., less than 0.5 microliter), in vitro, electrochemical sensors are used with Freestyle® and Freestyle Flash™ glucose meters (see http://abbottdiabetescare.com, which is hereby incorporated by reference). These test strip sensors generally include a working electrode on a first substrate, a counter (or counter/reference) electrode on a second substrate, and a sample chamber. The sample chamber is configured so that when a sample (e.g., of blood) is provided in the chamber, the sample is in electrolytic contact with both the working electrode, the counter electrode and any reference electrodes or indicator electrodes that may be present. This allows electrical current to flow between the electrodes to effect the electrolysis (electrooxidation or electroreduction) of the analyte. A spacer is generally positioned between first substrate and second substrate to provide a spacing between electrodes and to provide the sample chamber in which the sample to be evaluated is housed.

FIGS. 3A-3C illustrates one of these test strips (see U.S. Pat. No. 6,942,518, which is assigned to the same assignee as the present application, and is hereby incorporated by reference). This configuration is used for side-filling, and end-filling is an alternative. FIG. 3A illustrates a first substrate 340 with a working electrode 342. FIG. 3B illustrates a spacer 344 defining a channel 346. FIG. 3C (inverted with respect to FIGS. 3A and 3B) illustrates a second substrate 348 with three counter (or counter/reference) electrodes 350, 352, 354. This multiple counter electrode arrangement can provide a fill indicator function, as described below. The length of the channel 346 is typically defined by the two parallel cuts along the sides 356, 358 of the sensors.

Glucose test strip sensors can be manufactured adjacent to one another, as illustrated in FIGS. 4A-4B. Such positioning during manufacture produces less waste material. This often results in better efficiency as compared to other techniques, such as individually placing components within the individual channels of test strip sensors.

General Method for Manufacturing Glucose Sensors

FIGS. 4A-4B illustrate the processing of a sheet 1000 of test strips. Referring now to FIGS. 4A and 4B, one example of a method for making thin film sensors is generally described, and can be used to make a variety of sensor arrangements. When the three layers of the test strips of FIGS. 3A-3C, e.g., are assembled, a sensor is formed.

In FIGS. 4A and 4B, a substrate 400, such as a plastic substrate, is moving in the direction indicated by the arrow. The substrate 400 can be an individual sheet or a continuous roll on a web. Multiple sensors can be formed on a substrate 400 as sections 422 that have working electrodes thereon and sections 424 that have counter electrodes and indicator electrodes thereon. These working, counter and indicator electrodes are electrically connected to corresponding traces and contact pads. Typically, working electrode sections 422 are produced on one half of substrate 400 and counter electrode sections 424 are produced on the other half of substrate 400. In some embodiments, the substrate 400 can be scored and folded to bring the sections 422, 424 together to form the sensor. In some embodiments, as illustrated in FIG. 4A, the individual working electrode sections 422 can be formed next to or adjacent each other on the substrate 400, to reduce waste material. Similarly, individual counter electrode sections 424 can be formed next to or adjacent each other. In other embodiments, the individual working electrode sections 422 (and, similarly, the counter electrode sections 424) can be spaced apart, as illustrated in FIG. 4B.

Radio Frequency Identification (RFID)

RFID provides an advantageous technology for remotely storing and retrieving data using devices called RFID tags. A RFID tag is a small object, such as an adhesive sticker, that can be attached to or incorporated into a product. There are passive and active RFID tags. Passive RFID tags are small devices that are generally used at shorter range and for simpler tracking and monitoring applications than active tags. Passive tags generally act over ranges up to 3-5 meters, and a few hundred are typically readable simultaneously within three meters of a reader. Because they are powered by radio waves from RFID tag reader, passive tags do not use a battery. Therefore these devices are generally inexpensive and smaller than active tags, and can last long. Active RFID tags have a power source, such as a battery, and generally have longer range and larger memories than passive tags. For example, active tags generally act over ranges up to 100 meters, and thousands of tags are typically readable simultaneously within 100 meters of a reader. For more details on passive and active RFID tags, see http://RFID-Handbook.com, which is hereby incorporated by reference.

RFID System

An RFID system generally includes a RFID tag and RFID reader. A RFID tag includes an antenna and digital memory chip. A RFID reader, also called an interrogator, includes an antenna and a transceiver, and emits and receives RF signals. RFID readers can read tags and can typically write data into the tags. For example, FIG. 5 schematically illustrates component circuitry of a passive RFID tag. A transceiver/receiver 502 of a RFID reader 505 is directionally coupled 504 to an antenna 506 of the reader 505. An RFID transponder 510 includes an antenna 512 (e.g., a dipole antenna) and memory 514.

It is desired to incorporate RFID tag technology into glucose test strips, test strip vials and/or boxes of strips. It is also desired to incorporate RFID reader into glucose meters.

SUMMARY OF THE INVENTION

A glucose monitoring system includes a glucose sensor strip or package of strips. The strip includes a substrate and a glucose monitoring circuit that has electrodes and a bodily fluid application portion of selected chemical composition. An antenna is integrated with the glucose sensor strip. A RFID sensor chip is coupled with the glucose sensor strip and the antenna. The chip has a memory containing digitally-encoded data representing calibration and/or expiration date information for the strip.

The antenna may be a loop antenna that has a conducting loop extending around substantially a perimeter of the substrate and has two ends coupled with the chip. A RFID reader may read, power and/or program the chip. The RFID reader may be integrated with a glucose meter that has a port for inserting the strip and measuring a glucose level. Alternatively, a glucose meter may include a RFID reader as a component. The calibration and/or expiration date data may be automatically read when the strip is inserted into the port of the glucose meter. The chip may include a battery or other power source, or may be a passive chip. The memory may also contain data representing a lot number of the strip, manufacture date for the strip, a type of strip, and/or a calibration code. The RFID sensor chip may operate at 13.56 MHz. The calibration data may include chemical composition information for the strip for accurately computing a glucose level based on the chemical composition.

BRIEF DESCRIPTION OF THE DRAWINGS

FIGS. 3A-3C illustrate a conventional test strip.

DETAILED DESCRIPTION OF THE PREFERRED EMBODIMENTS

A RFID sensor is advantageously coupled with a blood glucose test strip or with a group of strips in accordance with a preferred embodiment. The RFID sensor preferably includes calibration and/or expiration date information for the strips. The calibration information preferably includes information relating to the chemical composition of the strip, so that a blood glucose reading can be accurately computed from a reading obtained using the strip with the particular chemical composition.

Figure 6:
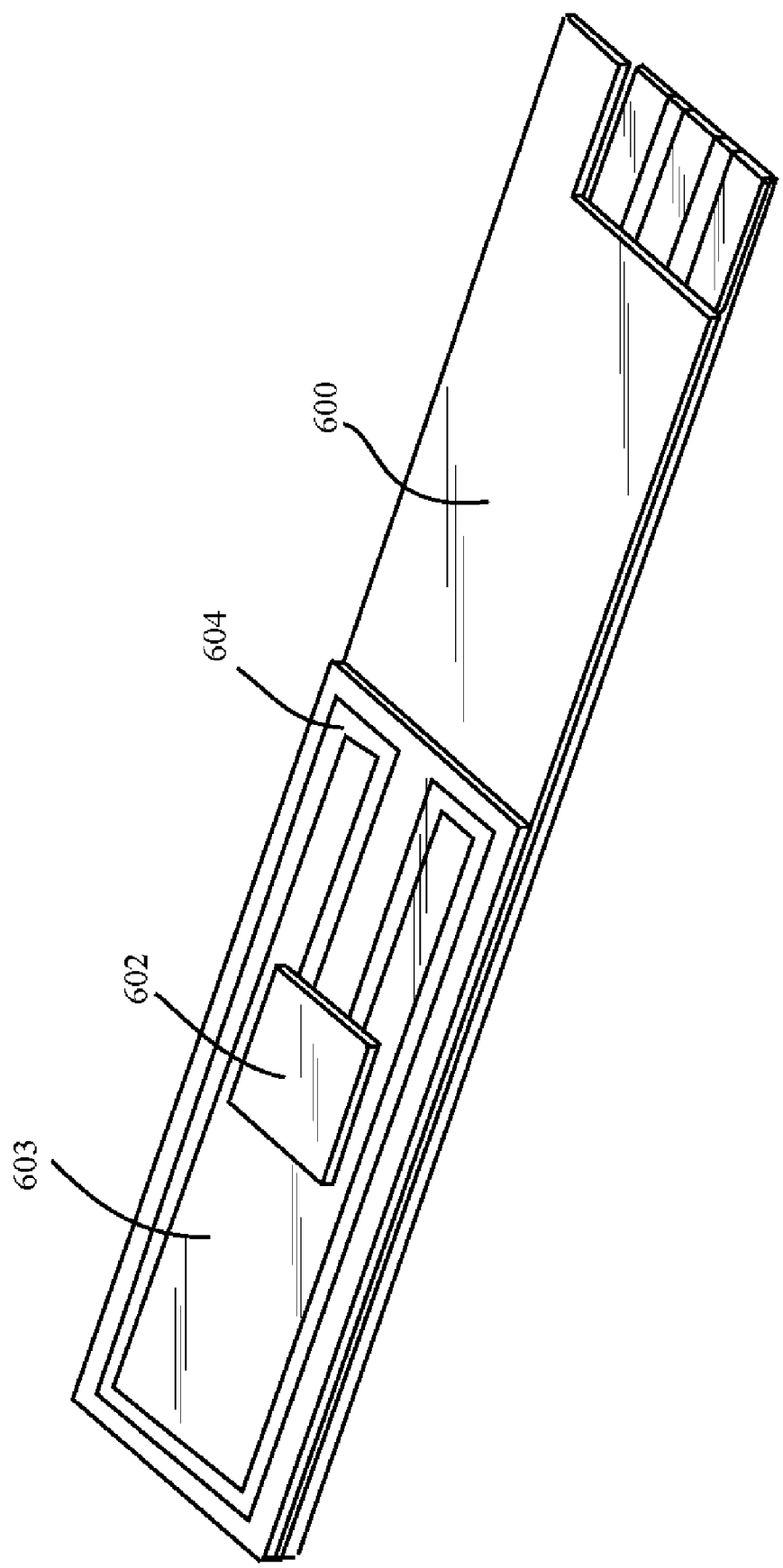
FIG. 6 illustrates a glucose test strip including a RFID chip and antenna in accordance with a preferred embodiment.

In one embodiment, an individual strip includes a RFID sensor. FIG. 6 illustrates a glucose test strip 600, e.g., a Freestyle® test strip manufactured by Abbott Diabetes Care of Alameda, Calif., that includes a RFID chip 602, which is mounted on a PCB substrate 603 or other suitable substrate, and an antenna 604, in accordance with a preferred embodiment. The antenna 604 may be a loop antenna, or a dipole antenna, or another antenna configuration.

Figure 7:
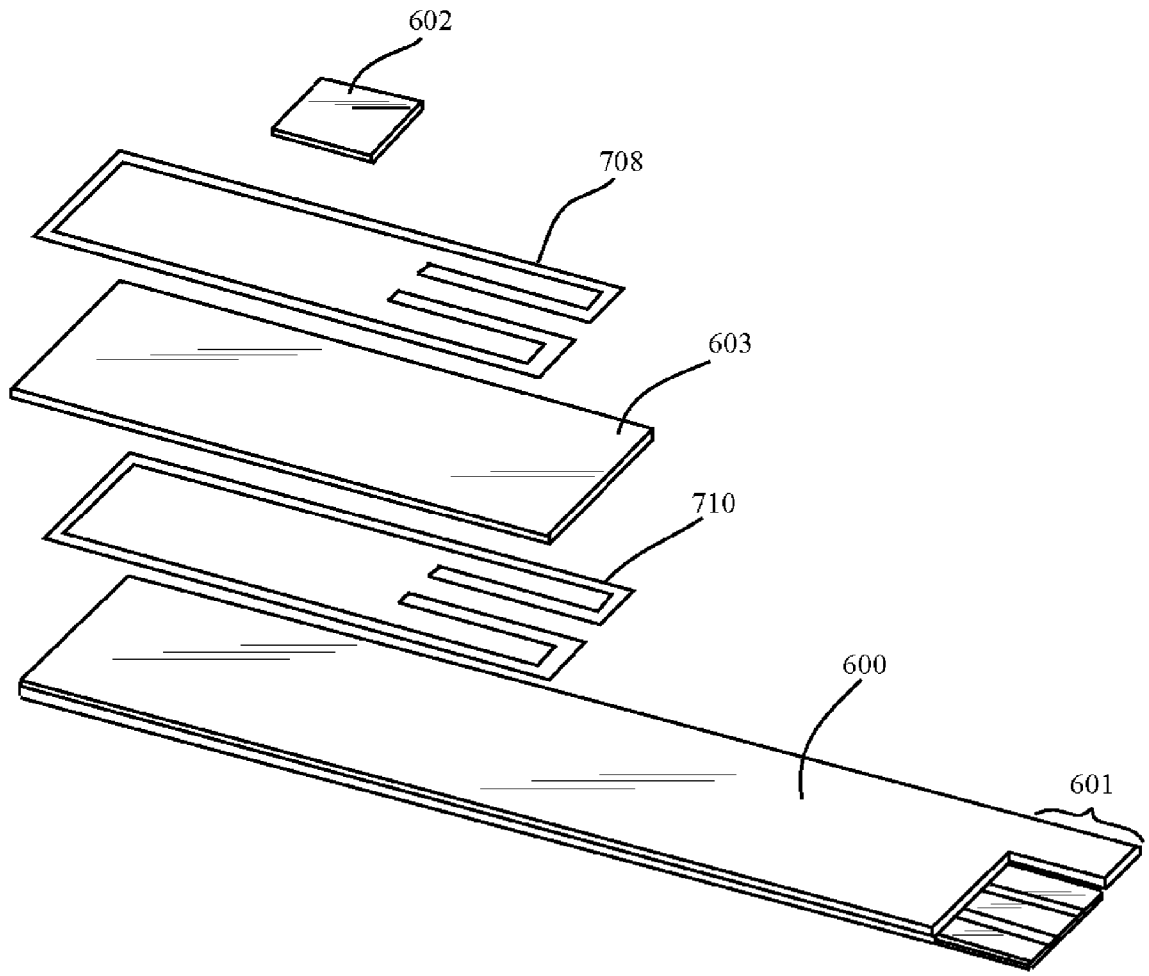
FIG. 7 is an exploded view of a glucose test strip in accordance with a preferred embodiment.
Figure 8:
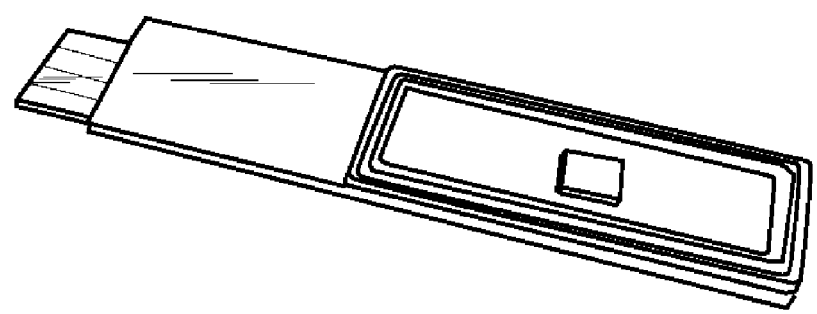
FIG. 8 illustrates a RFID chip mounted on a glucose test strip in accordance with a preferred embodiment.

FIG. 7 is an exploded view of a Freestyle® or other glucose test strip 600 including a sample application end 601, with sample chamber and electrodes, a RFID chip 602 in accordance with a preferred embodiment. The RFID chip 602 is mounted on a PCB substrate 603 that is attached to, integral with or part of the strip 600. There is a top-side loop antenna 708 and a bottom side loop antenna 710. FIG. 8 illustrates a RFID chip 602 mounted on a glucose test strip 600 in accordance with another embodiment.

Figure 9:
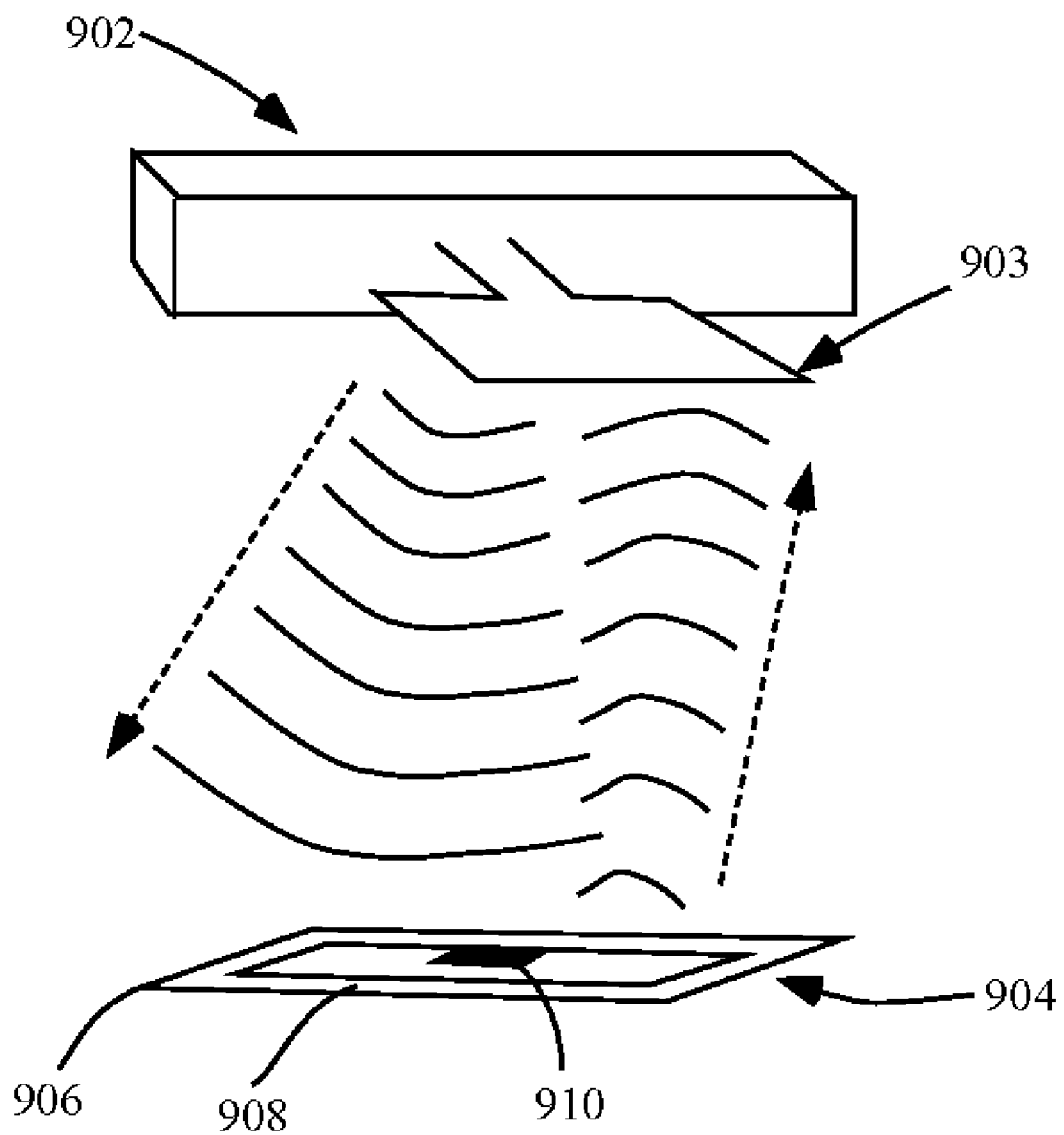
FIG. 9 illustrates a communication system including a glucose test strip and a RFID reader in accordance with a preferred embodiment.

Preferably a RFID reader programs the RFID sensor with the calibration data and/or powers the RFID sensor. The RFID reader may be integrated with a blood glucose meter, or the meter may include an RFID reader as a component. FIG. 9 illustrates a communication system including a RFID reader 902 and a tag 904 in accordance with a preferred embodiment. The reader 902 includes a reader antenna 903. The tag 904 may be coupled with a glucose test strip or with a package or box of strips. The tag 904 includes a substrate 906, tag antenna 908 and RFID chip 910. The reader 902 sends a radio wave that impinges upon the tag 904. A backscattering radio wave is propagated back from the tag 904 as a result.

Figure 10:
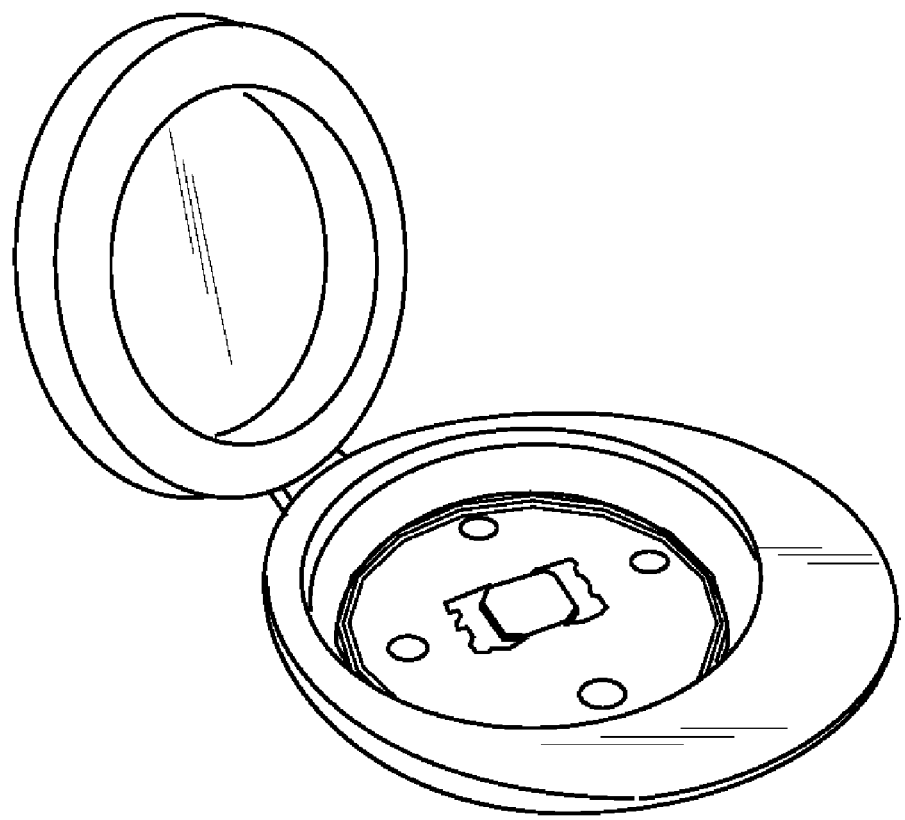
FIG. 10 illustrates a RFID chip mounted on a package for holding glucose test strips in accordance with a preferred embodiment.

FIG. 10 illustrates a RFID chip mounted on a package for holding glucose test strips in accordance with a preferred embodiment. The package illustrated is a lid of a vial container of several tens of test strips. Preferably, each of the test strips in the vial was manufactured on a same sheet of strips, such that the chemical compositions of the strips are very similar and that the strips have a common expiration date.

Meters Equipped with a RFID Tag Reader (or Vice-Versa)

In accordance with another advantageous embodiment, a RFID tag reader or interrogator may be adapted for providing glucose testing. As such, a test strip receptacle and glucose measurement circuitry and/or programming may be provided in a glucose meter module that plugs into a RFID reader device or is integrated therein or otherwise communicates data and/or power by cable or multi-pin connection, or wirelessly (at least for the data communication) with the RFID reader. The glucose meter module can use the power and processing capabilities of the reader, thus streamlining the meter module compared with a stand-alone meter. Even data storage for both the reader and meter may be combined into one location or otherwise synchronized.

In another embodiment, a glucose meter may be adapted for providing RFID reading and/or writing. A RFID reader may be provided that plugs into a glucose meter or is integrated therein or otherwise communicates data and/or power by cable, or multi-pin connection, or wirelessly (at least for the data communication) with the glucose meter. The RFID reader can use the power and processing capabilities of the meter, thus streamlining the RFID reader module compared with a stand-alone reader. Even data storage for both the reader and meter may be combined into one location or otherwise synchronized.

Human errors are advantageously prevented by automatically retrieving a calibration code of one or more test strips stored in a RFID tag. Expiration date information for the test strip can also be detected from the tag. Different types of test strips can also be detected, which is advantageous particularly for different strips that appear alike and/or that may be used with a same piece of diabetes care equipment. Several other possible types of data may be stored in and read from a RFID tag, which may used alone and/or may be combined with other diabetes care data to enhance the reliability of a diabetes treatment regimen, including the recording, retrieval and/or use of relevant data (see, e.g., U.S. patent application Ser. Nos. 10/112,671 and 11/146,897, which are assigned to the same assignee and are hereby incorporated by reference). Embodiments disclosed in the Ser. No. 10/112,671 application, and in U.S. Pat. Nos. 5,899,855, 5,735,285, 5,961,451, 6,159,147 and 5,601,435, which are hereby incorporated by reference, describe alternative arrangements for combining functionalities of devices that may be modified for use with an advantage glucose meter and RFID reader combination in accordance with a preferred embodiment.

Figure 11:
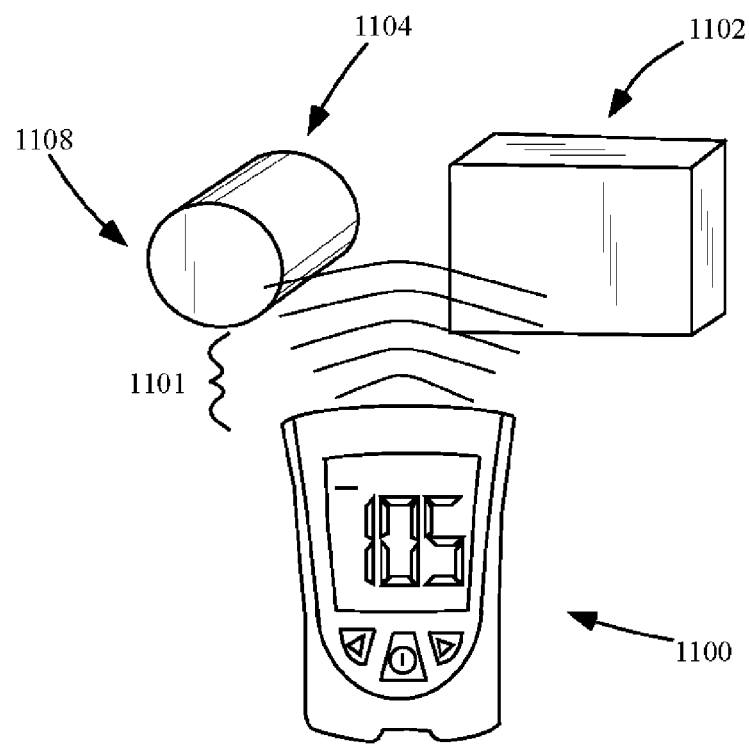
FIG. 11 illustrates a glucose meter communicating with a RFID tag that is mounted on a package or box of glucose test strips in accordance with a preferred embodiment.

FIG. 11 illustrates a glucose meter 1100 sending radio waves 1101 for communicating with a RFID tag (not specifically shown) that is mounted on a package such as a vial 1104 or a box 1106 of glucose test strips in accordance with preferred embodiments. In a first embodiment, a RFID sensor is coupled with a package or vial container 1104 of glucose test strips. The container 1104 may have a lid 1108 with the RFID sensor attached on its inside surface, or embedded therein, or mounted on the outside with a protective layer affixed over it, or alternatively on the bottom of the container 1104 or otherwise. In another embodiment, the strips are contained within a box 1102 having a RFID tag mounted preferably on the inside of the box to protect the tag, or alternatively on the outside having a protective layer over it.

Figure 12:
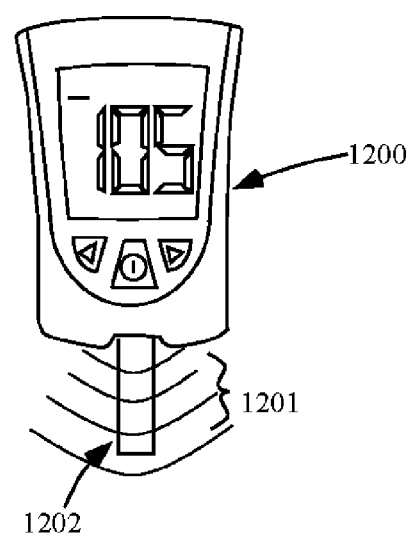
FIG. 12 illustrates a glucose meter communicating with a RFID tag that is mounted on a glucose test strip in accordance with a preferred embodiment.

Containers 1102 or 1104 preferably include only strips from a same sheet of strips having same or similar chemical compositions and expiration dates. One strip may be tested from the sheet, while the remaining strips are placed into the container. The rest of the strips that are placed in the container and not tested will reliably have the same or very similar chemical composition as the tested strip. The RFID sensor may be read only, or may also be write programmable. The data contained within the memory of the RFID sensor preferably includes calibration data regarding the chemical compositions of the strips in the container 1102, 1104 which are each estimated to have the same chemical composition as the test strip, and expiration date data for the strips, which should be the same for all of the strips that were manufactured on the same sheet at the same time. In accordance with another embodiment, FIG. 12 illustrates a glucose meter 1200 communicating with a RFID tag using radio waves 1201 that is mounted on a glucose test strip 1202 in accordance with a preferred embodiment.

RFID Frequency Band Allocation

Multiple frequency bands are available for RFID communication in accordance with preferred embodiments. For example, there is a low frequency band around 125 kHz-134 kHz. There is a worldwide standard high frequency band around 13.56 MHz. There are also UHF frequency bands around 868 MHz for European Union countries, and around 902 MHz-928 MHz for the United States. There is also a microwave frequency band around 2.45 GHz.

It is preferred to use the worldwide standard around 13.56 MHz as the frequency band of operation in accordance with a preferred embodiment. This is the most popular frequency band, and a silicon-based RFID chip operating at this frequency band may be provided at low cost. This frequency band has a high efficiency RF energy transition, and complies with a world-wide RF standard.

Test Strip Coding and Meter Calibrating

Test strip coding and meter calibrating are the processes by which a blood glucose meter is matched with the reactivity of the test strips. A glucose meter will calculate a glucose level of a fluid applied to a strip based on a predetermined chemical composition of the strip. If the predetermined composition varies from the actual composition, then glucose test results provided by the meter will also vary from actual glucose levels.

Figure 1:
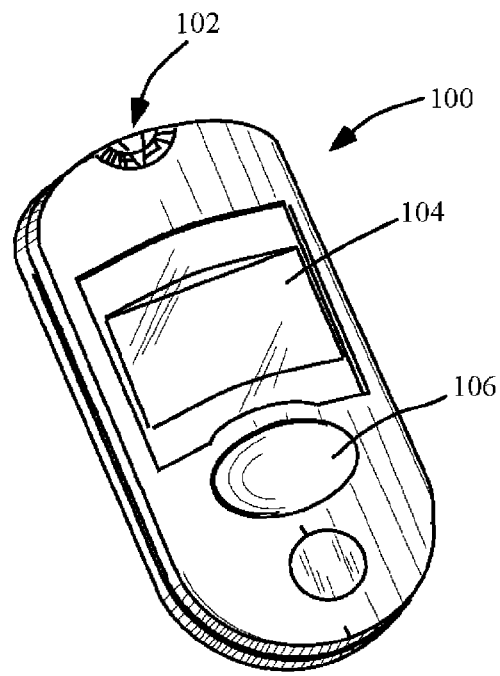
FIG. 1 illustrates a conventional blood glucose meter.
Figure 2:
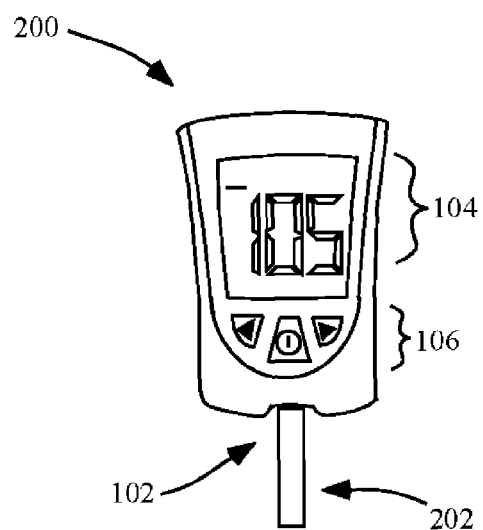
FIG. 2 illustrates a blood glucose meter having a strip inserted into a slot for testing a body fluid sample applied to the strip.
Figure 4A:
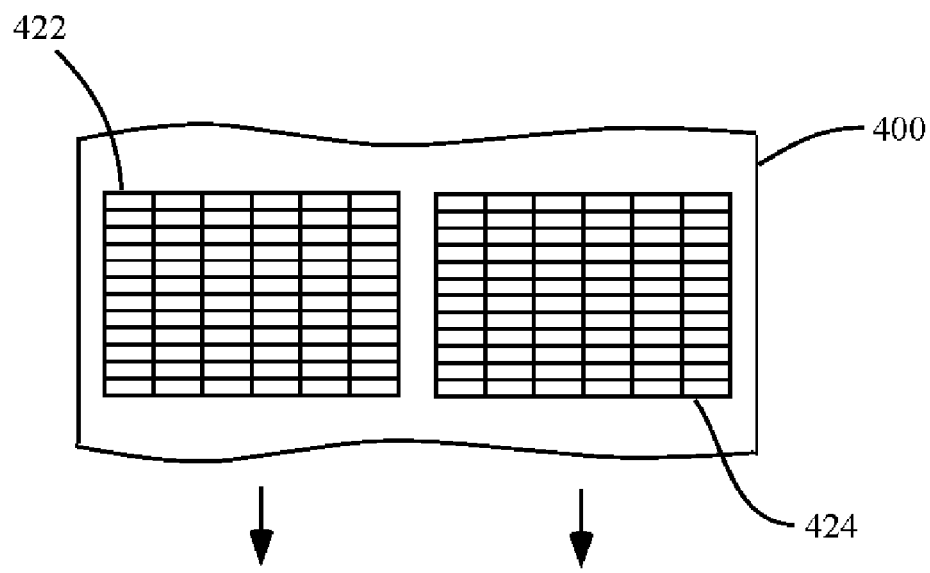
FIGS. 4A-4B illustrate the processing of a sheet of test strips.
Figure 4B:
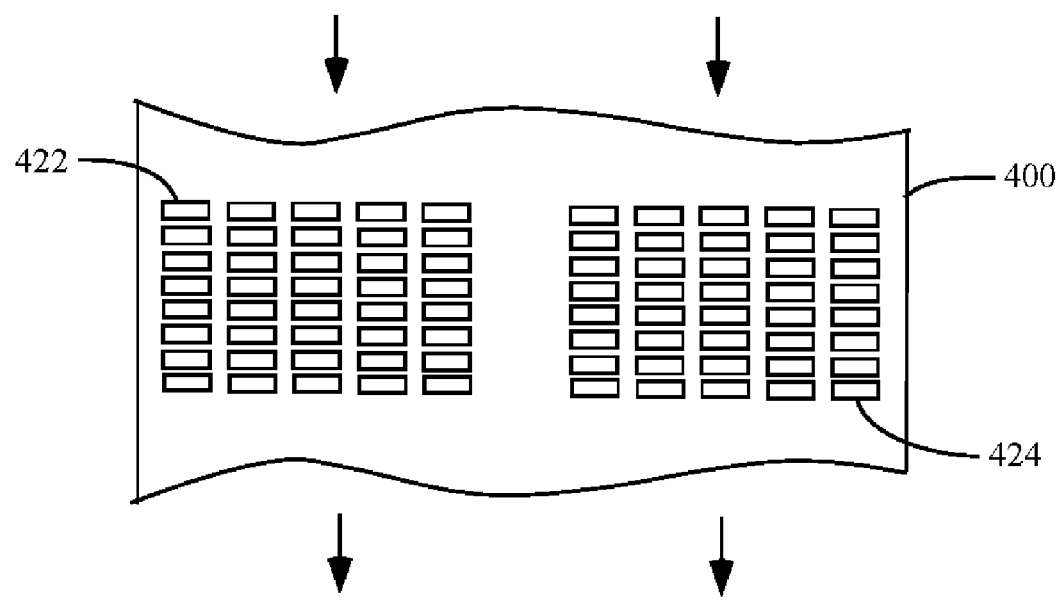
Figure 5:
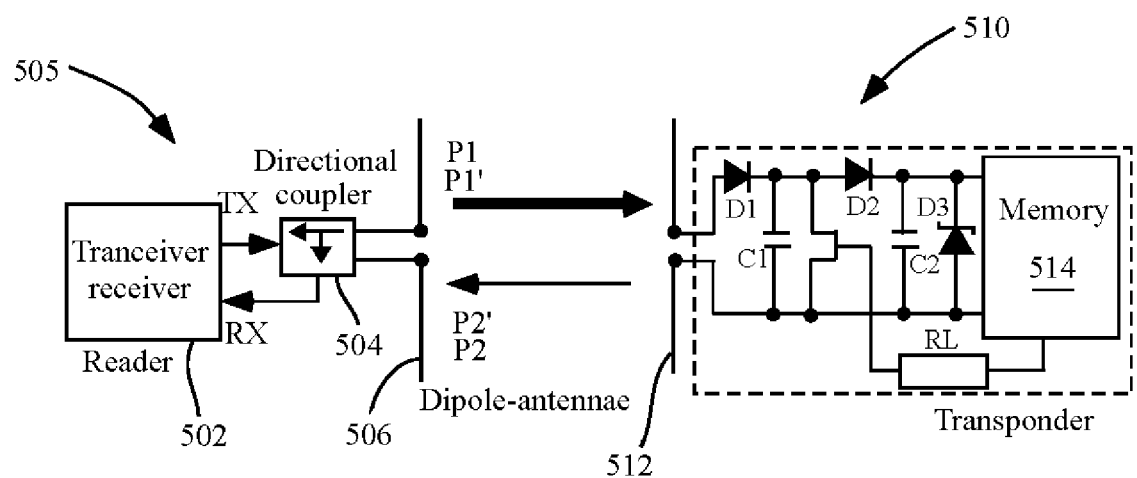
FIG. 5 illustrates a conventional passive RFID tag.

Even test strips intended to be manufactured with a same chemical composition can vary based on uncertainties in the manufacturing process. Although this variance may be only very small when great care is taken in the manufacturing process, these very small variances can alter glucose measurement results that are output by a glucose meter from actual values unless the meter is properly calibrated. As illustrated at FIGS. 4A-4B and described briefly above, multiple test strips are advantageously manufactured together on a same sheet. Test strips that are manufactured on a same sheet have reduced variances in chemical composition compared with test strip manufactured separately. Therefore, one strip from a sheet is advantageously tested in accordance with a preferred embodiment to determine its precise composition. Then, blood glucose meters are calibrated according to that composition when utilizing other strips from that same sheet for testing. As a consequence, glucose testing results are more reliably precise and accurate.

To ensure this precision and accuracy of glucose test results using blood glucose meters in accordance with a preferred embodiment, the strips may be coded, e.g., by the strip manufacturer before they are shipped out. In addition, the glucose meter is calibrated. Calibration of the meter can be performed by inserting a code strip into the meter and executing a calibration routine. The Precision™ meter of Abbott Diabetes Care® preferably uses this technique. Another method of calibration can be performed by entering a code number into the meter. This technique is preferred for use with the Freestyle® meter also of Abbott Diabetes Care®. Advantageously, the encoded calibration data can be stored in the RFID chip described above that is affixed to a strip, or a vial, box or other container of strips. Enhanced efficiency and reliability is achieved whether an RFID chip is mounted to each strip or to a vial, box or other container of strips. However, when the RFID chip from which the encoded calibration data is read is affixed to the vial, box or other container of strips, and preferably all of the strips within that vial, box or other container were manufactured from the same sheet of strips, as described above, then even greater efficiency, i.e., programming and use of a reduced number of RFID chips, is achieved. Advantageously, one RFID chip may be used for initially programming and for later obtaining calibration data for multiple strips. Moreover, expiration date data may be stored and obtained in RFID chips with the same efficiencies and advantages.

It is preferred to provide passive RFID tags on test strips, vials, boxes and/or other containers of strips. The preferred passive RFID tags can store approximately two kilobytes of data or more. The memory of the passive tag can be read and written repeatedly. In the memory, the following are preferably stored: test strip calibration codes, lot number, manufacture date, expiration date, other calibration information, or type of strip, or combinations thereof.

By using RFID tags, a test strip manufacturing process is advantageously upgraded. IN this embodiment, test strips are manufactured and preferably packed directly into final packages in vials or boxes or other containers, instead of waiting, e.g., for two weeks, for labeling of calibration codes. The calibration codes are preferably written into the RFID tags after the codes are determined. A lot group size of the test strips can be broken into a smaller geometry to achieve a more precise uniformity of chemical reactivity code. Further data can be stored into RFID tags, as desired.

The calibration date, expiration date and/or other diabetes care information may be provided in a RFID chip or module associated with glucose sensors other than test strips and test strip containers. For example, continuous glucose sensors that may be implanted or partially in vivo or otherwise can include RFID features described otherwise herein. In addition, diabetes care devices other than glucose sensors such as insulin pumps can use the RFID communication of data such as pump calibration data, insulin infusion data, computed or received dose data or glucose data available at the pump. As to the latter feature, glucose data may be communicated to a pump by a glucose meter, and then read by a RFID reader.

The present invention is not limited to the embodiments described above herein, which may be amended or modified without departing from the scope of the present invention as set forth in the appended claims, and structural and functional equivalents thereof.

In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, all references cited above herein, in addition to the background and summary of the invention sections, are hereby incorporated by reference into the detailed description of the preferred embodiments as disclosing alternative embodiments and components.

We claim:

1. An analyte monitoring system, comprising:
an analyte sensor;
an antenna integrated with the analyte sensor;
a radio frequency identification (RFID) sensor chip coupled with the analyte sensor and the antenna, the RFID sensor chip including a memory for storing digitally-encoded data representing a monitored analyte level detected by the analyte sensor; and
an RFID reader coupled to a housing and configured to transmit an radio frequency (RF) signal and to receive data from the RFID sensor chip, the RFID reader further configured to provide an RF power signal;
wherein the digitally encoded data representing the monitored analyte level is detected by the RFID reader based a backscattering radio wave from the RFID sensor chip when the RFID reader is positioned within a predetermined distance from the RFID sensor chip.

2. The system of claim 1, wherein the antenna comprises one of a loop antenna or a dipole antenna.

3. The system of claim 2, wherein the loop antenna comprises a conducting loop.

4. The system of claim 3, wherein the conducting loop is disposed substantially around a perimeter of a circuit board electrically coupled to the analyte sensor.

5. The system of claim 1, wherein the RFID reader housing includes a strip port.

6. The system of claim 5, wherein the strip port is configured to receive an in vitro glucose test strip.

7. The system of claim 6, wherein the analyte sensor is calibrated based on a blood glucose measurement from the in vitro glucose test strip.

8. The system of claim 1, wherein the RFID reader housing includes a blood glucose meter.

9. The system of claim 1, wherein the memory further stores data representing one or more of a lot information associated with the analyte sensor, a calibration code associated with the analyte sensor, or an analyte sensor expiration information.

10. The system of claim 1, wherein the RFID sensor chip propagates a backscattering radio wave when the RFID reader is positioned within the predetermined distance and within the RF power signal range from the RFID sensor chip.

11. The system of claim 1, wherein the predetermined distance includes approximately 5 inches or less.

12. The system of claim 1, wherein the RFID sensor chip and the RFID reader operate in an ultra high frequency (UHF) frequency band.

13. The system of claim 1 further including an output unit coupled to the RFID reader housing for outputting information associated with the monitored analyte level.

14. The system of claim 13, wherein the output unit includes a display for displaying an indication related to the monitored analyte level.

15. The system of claim 14, wherein the displayed indication includes a numerical value of the analyte level monitored by the analyte sensor.

16. The system of claim 1, wherein the digitally encoded data representing the monitored analyte level includes a current analyte level data and one or more prior analyte level data stored in the memory.

17. The system of claim 1, wherein the plurality of electrodes includes one or more of a working electrode, a counter electrode or a reference electrode.

18. The system of claim 1, wherein the analyte sensor is an in vivo glucose sensor.

19. The system of claim 1, further comprising a second antenna integrated with the analyte sensor and coupled with the RFID sensor chip, wherein the antenna and the RFID sensor chip are disposed on a first surface of a printed circuit board substrate and the second antenna is disposed on a second surface of the printed circuit board substrate.

20. A method, comprising:
positioning a radio frequency identification (RFID) reader within a predetermined distance from an RFID sensor chip in electrical contact with an analyte sensor;
transmitting a radio frequency (RF) signal including a power signal; and
detecting a backscattering radio wave from the RFID sensor chip including digitally encoded data representing an analyte level monitored by the analyte sensor.

21. The method of claim 20 including outputting information associated with the digital encoded data.

22. The method of claim 21, wherein outputting information includes displaying a glucose value associated with the digitally encoded data.

23. The method of claim 20 including storing the digitally encoded data.

24. The method of claim 20 further including:
receiving a blood glucose measurement from an in vitro test strip; and
calibrating the analyte sensor based on the received blood glucose measurement.

* * * * *

UNITED STATES PATENT AND TRADEMARK OFFICE
CERTIFICATE OF CORRECTION

| | |
|---|---|
| PATENT NO. | : 8,115,635 B2 |
| APPLICATION NO. | : 12/625528 |
| DATED | : February 14, 2012 |
| INVENTOR(S) | : Timothy T. Goodnow and Lei He |

It is certified that error appears in the above-identified patent and that said Letters Patent is hereby corrected as shown below:

Specification
Column 2, line 8: replace "sheet 1000 of" with --sheet of--.
Column 5, line 28: replace "box 1106 of" with --box 1102 of--.

Claims
Column 7, lines 56-57, in Claim 1: change "based a backscattering" to --based on a backscattering--.
Column 8, line 14, in Claim 10: change "propagates a backscattering" to --propagates the backscattering--.

Signed and Sealed this
Twelfth Day of July, 2016

Michelle K. Lee
*Director of the United States Patent and Trademark Office*